United States Patent
Wortley et al.

(10) Patent No.: US 10,597,617 B2
(45) Date of Patent: *Mar. 24, 2020

(54) CLEANING COMPOSITION THAT PROVIDES RESIDUAL BENEFITS

(71) Applicant: S. C. Johnson & Son, Inc., Racine, WI (US)

(72) Inventors: Russell B. Wortley, Kenosha, WI (US); Michael E. Klinkhammer, Dunedin, FL (US); John R. Wietfeldt, Franksville, WI (US); Francis J. Randall, Racine, WI (US)

(73) Assignee: S. C. Johnson & Son, Inc., Racine, WI (US)

(*) Notice: Subject to any disclaimer, the term of this patent is extended or adjusted under 35 U.S.C. 154(b) by 881 days.

This patent is subject to a terminal disclaimer.

(21) Appl. No.: 15/205,232

(22) Filed: Jul. 8, 2016

(65) Prior Publication Data

US 2016/0340621 A1  Nov. 24, 2016

Related U.S. Application Data

(63) Continuation of application No. 12/461,103, filed on Jul. 31, 2009, now Pat. No. 9,410,111, which is a continuation-in-part of application No. 12/388,588, filed on Feb. 19, 2009, now abandoned.

(60) Provisional application No. 61/064,181, filed on Feb. 21, 2008.

(51) Int. Cl.

| | |
|---|---|
| *C11D 1/72* | (2006.01) |
| *C11D 17/00* | (2006.01) |
| *C11D 1/29* | (2006.01) |
| *C11D 1/83* | (2006.01) |
| *C11D 3/18* | (2006.01) |
| *C11D 3/20* | (2006.01) |
| *C11D 3/50* | (2006.01) |
| *C11D 1/825* | (2006.01) |
| *C11D 11/00* | (2006.01) |
| *C11D 1/12* | (2006.01) |
| *C11D 1/66* | (2006.01) |
| *C11D 1/722* | (2006.01) |
| *C11D 1/75* | (2006.01) |

(52) U.S. Cl.
CPC .............. *C11D 17/003* (2013.01); *C11D 1/29* (2013.01); *C11D 1/72* (2013.01); *C11D 1/8255* (2013.01); *C11D 1/8305* (2013.01); *C11D 3/18* (2013.01); *C11D 3/2013* (2013.01); *C11D 3/2068* (2013.01); *C11D 3/50* (2013.01); *C11D 11/0023* (2013.01); *C11D 17/0056* (2013.01); *C11D 1/123* (2013.01); *C11D 1/662* (2013.01); *C11D 1/722* (2013.01); *C11D 1/75* (2013.01)

(58) Field of Classification Search
CPC ................................ C11D 17/003; C11D 1/29
See application file for complete search history.

(56) References Cited

U.S. PATENT DOCUMENTS

| | | |
|---|---|---|
| 2,695,735 A | 11/1954 | von Doornik |
| 3,273,760 A | 9/1966 | Frankenberg |
| 3,346,147 A | 10/1967 | Higgins et al. |
| 3,578,499 A | 5/1971 | Crotty et al. |
| 3,639,574 A | 2/1972 | Schmolka |
| 3,681,141 A | 8/1972 | Muoio et al. |
| 3,955,986 A | 5/1976 | Miller |
| 4,226,736 A | 10/1980 | Bush et al. |
| 4,314,991 A | 2/1982 | Sipos |
| 4,396,520 A | 8/1983 | Payne et al. |
| 4,396,599 A | 8/1983 | Sipos |
| 4,474,678 A | 10/1984 | Lutz et al. |
| 4,483,780 A | 11/1984 | Llenado |
| 4,521,326 A | 6/1985 | Seibert et al. |
| 4,536,317 A | 8/1985 | Llenado et al. |
| 4,540,510 A | 9/1985 | Karl |
| 4,578,207 A | 3/1986 | Holdt et al. |
| 4,595,527 A | 6/1986 | Gipp |
| 4,610,799 A | 9/1986 | Wilsberg et al. |
| 4,636,256 A | 1/1987 | Valone |
| 4,668,423 A | 5/1987 | Drozd et al. |
| 4,681,704 A | 7/1987 | Bernardino et al. |
| 4,683,072 A | 7/1987 | Holdt et al. |
| 4,696,757 A | 9/1987 | Blank et al. |
| 4,765,844 A | 8/1988 | Merrem et al. |
| 4,767,625 A | 8/1988 | Mitsuno et al. |
| 4,772,427 A | 9/1988 | Dawson et al. |
| 4,774,017 A | 9/1988 | Seibert et al. |
| 4,803,012 A | 2/1989 | Wershofen |
| 4,824,763 A | 4/1989 | Lee |
| 4,836,951 A | 6/1989 | Totten et al. |
| 4,880,568 A | 11/1989 | Staley et al. |
| 4,911,858 A | 3/1990 | Bunczk et al. |
| 4,938,888 A | 7/1990 | Kiefer et al. |
| 4,965,009 A | 10/1990 | Baur et al. |
| 4,994,266 A | 2/1991 | Wells |

(Continued)

FOREIGN PATENT DOCUMENTS

| | | |
|---|---|---|
| AU | 8138491 B | 11/1991 |
| DE | 19715872 A1 | 10/1998 |
| DE | 10047298 A1 | 4/2002 |
| DE | 10356254 A1 | 10/2004 |
| EP | 0386960 A2 | 9/1990 |
| EP | 0631788 A1 | 1/1995 |
| EP | 0864637 A1 | 9/1998 |
| EP | 1029911 A1 | 8/2000 |
| EP | 1086199 B1 | 5/2002 |
| EP | 1318191 A1 | 6/2003 |

(Continued)

*Primary Examiner* — Monique R Peets

(57) ABSTRACT

A composition for use on a hard surface. The composition has: (i) at least 7.5 wt. % of at least one surfactant selected; (ii) a blend of linear primary alcohols, or a blend of ethoxylated linear primary alcohols, wherein each alcohol of the non-ethoxylated blend or ethoxylated blend includes a carbon chain containing 9-17 carbons; (iii) a transport rate factor of less than about 55 seconds; and (iv) an adhesion time of greater than about 8 hours.

26 Claims, 15 Drawing Sheets

(56) References Cited

U.S. PATENT DOCUMENTS

| | | |
|---|---|---|
| 5,041,230 A | 8/1991 | Borcher, Sr. et al. |
| 5,043,091 A | 8/1991 | Joshi et al. |
| 5,047,167 A | 9/1991 | Steyn et al. |
| 5,049,299 A | 9/1991 | Bunczk et al. |
| 5,075,040 A | 12/1991 | Rivenaes |
| 5,076,954 A | 12/1991 | Loth et al. |
| 5,082,584 A | 1/1992 | Loth et al. |
| 5,093,014 A | 3/1992 | Neillie |
| 5,096,621 A | 3/1992 | Tosaka et al. |
| 5,100,574 A | 3/1992 | Urushibata et al. |
| 5,108,643 A | 4/1992 | Loth et al. |
| 5,139,705 A | 8/1992 | Wittpenn, Jr. et al. |
| 5,183,601 A | 2/1993 | Jisai et al. |
| 5,205,955 A | 4/1993 | Bunczk et al. |
| 5,217,710 A | 6/1993 | Williams et al. |
| 5,246,694 A | 9/1993 | Birthwistle |
| 5,254,290 A | 10/1993 | Blandiaux et al. |
| 5,336,427 A | 8/1994 | Bunczk et al. |
| 5,341,557 A | 8/1994 | Perlman |
| 5,352,389 A | 10/1994 | Gazzani |
| 5,370,816 A | 12/1994 | Balzer et al. |
| 5,372,803 A | 12/1994 | Williams et al. |
| 5,374,372 A | 12/1994 | Broze et al. |
| 5,376,298 A | 12/1994 | Michael |
| 5,382,376 A | 1/1995 | Michael et al. |
| 5,393,468 A | 2/1995 | Erilli et al. |
| 5,449,763 A | 9/1995 | Wulff et al. |
| 5,460,742 A | 10/1995 | Cavanagh et al. |
| 5,466,395 A | 11/1995 | Tosaka et al. |
| 5,472,629 A | 12/1995 | Lysy et al. |
| 5,478,554 A | 12/1995 | Behler et al. |
| 5,490,948 A | 2/1996 | Klier et al. |
| 5,523,014 A | 6/1996 | Dolan et al. |
| 5,536,332 A | 7/1996 | Chun |
| 5,538,662 A | 7/1996 | Klier et al. |
| 5,540,853 A | 7/1996 | Trinh et al. |
| 5,549,842 A | 8/1996 | Chang |
| 5,556,628 A | 9/1996 | Derian et al. |
| 5,556,835 A | 9/1996 | Inaoka et al. |
| 5,559,091 A | 9/1996 | Geboes et al. |
| 5,562,850 A | 10/1996 | Woo et al. |
| 5,562,912 A | 10/1996 | Burke et al. |
| 5,565,421 A | 10/1996 | Aszman et al. |
| 5,591,376 A | 1/1997 | Kiewert et al. |
| 5,593,958 A | 1/1997 | Mondin et al. |
| 5,597,792 A | 1/1997 | Klier et al. |
| 5,597,793 A | 1/1997 | Besse et al. |
| 5,656,580 A | 8/1997 | Carrie et al. |
| 5,668,094 A | 9/1997 | Bacon et al. |
| 5,681,801 A | 10/1997 | Zocchi |
| 5,691,289 A | 11/1997 | Purcell et al. |
| 5,705,470 A | 1/1998 | Faris |
| 5,707,948 A | 1/1998 | Evers et al. |
| 5,709,852 A | 1/1998 | Gopalkrishnan et al. |
| 5,728,393 A | 3/1998 | Soudant et al. |
| 5,756,437 A | 5/1998 | Yamazaki et al. |
| 5,763,386 A | 6/1998 | Mondin et al. |
| 5,780,404 A | 7/1998 | Bacon et al. |
| 5,792,737 A | 8/1998 | Gruning et al. |
| 5,811,383 A | 9/1998 | Klier et al. |
| 5,827,810 A | 10/1998 | Brodbeck et al. |
| 5,849,310 A | 12/1998 | Trinh et al. |
| 5,851,971 A | 12/1998 | Durbut et al. |
| 5,851,979 A | 12/1998 | Scialla et al. |
| 5,854,194 A | 12/1998 | Davister et al. |
| 5,863,521 A | 1/1999 | Schaefer et al. |
| 5,866,527 A | 2/1999 | Mertens |
| 5,877,135 A | 3/1999 | Hahn |
| 5,908,617 A | 6/1999 | Moore et al. |
| 5,916,549 A | 6/1999 | Beauquey et al. |
| 5,922,665 A | 7/1999 | Liu |
| 5,929,010 A | 7/1999 | Kellett et al. |
| 5,929,014 A | 7/1999 | Beaujean et al. |
| 5,929,022 A | 7/1999 | Velaquez |
| 5,945,390 A | 8/1999 | Veltman et al. |
| 5,948,741 A | 9/1999 | Ochomogo et al. |
| 5,952,287 A | 9/1999 | Gross et al. |
| 5,958,858 A | 9/1999 | Bettiol et al. |
| 5,962,392 A | 10/1999 | Revell et al. |
| 5,965,502 A | 10/1999 | Balzer |
| 5,972,869 A | 10/1999 | Cao et al. |
| 5,977,050 A | 11/1999 | Faris |
| 5,981,458 A | 11/1999 | Crutcher et al. |
| 5,981,466 A | 11/1999 | Morelli et al. |
| 5,985,808 A | 11/1999 | He et al. |
| 6,001,789 A | 12/1999 | Trinh et al. |
| 6,004,915 A | 12/1999 | Elliott et al. |
| 6,020,296 A | 2/2000 | Mertens et al. |
| 6,022,839 A | 2/2000 | Durbut et al. |
| 6,030,936 A | 2/2000 | Lu et al. |
| 6,034,044 A | 3/2000 | Scheper et al. |
| 6,043,208 A | 3/2000 | Durbut et al. |
| 6,048,831 A | 4/2000 | Mori et al. |
| 6,077,318 A | 6/2000 | Trinh et al. |
| 6,080,706 A | 6/2000 | Blanvalet et al. |
| 6,080,712 A | 6/2000 | Revell et al. |
| 6,087,309 A | 7/2000 | Vinson et al. |
| 6,100,228 A | 8/2000 | Argo et al. |
| 6,103,681 A | 8/2000 | Chantler et al. |
| 6,140,284 A | 10/2000 | Cheung et al. |
| 6,140,296 A | 10/2000 | Ishii et al. |
| 6,140,297 A | 10/2000 | Ishii et al. |
| 6,150,318 A | 11/2000 | Silvester et al. |
| 6,150,321 A | 11/2000 | Davister et al. |
| 6,153,571 A | 11/2000 | Komocki et al. |
| 6,153,572 A | 11/2000 | Stamm |
| 6,169,060 B1 | 1/2001 | Taniuchi |
| 6,177,389 B1 | 1/2001 | Morelli et al. |
| 6,177,394 B1 | 1/2001 | Durbut et al. |
| 6,191,083 B1 | 2/2001 | Brooks et al. |
| 6,207,139 B1 | 3/2001 | Lee et al. |
| 6,207,631 B1 | 3/2001 | Kasturi et al. |
| 6,221,822 B1 | 4/2001 | Crutcher et al. |
| 6,239,093 B1 | 5/2001 | Foley et al. |
| 6,248,135 B1 | 6/2001 | Trinh et al. |
| 6,248,705 B1 | 6/2001 | Cardola et al. |
| 6,248,708 B1 | 6/2001 | Merz et al. |
| 6,264,961 B1 | 7/2001 | Ansmann et al. |
| 6,294,510 B1 | 9/2001 | Norman et al. |
| 6,329,333 B1 | 12/2001 | Merz et al. |
| 6,336,977 B1 | 1/2002 | Menke et al. |
| 6,342,206 B1 | 1/2002 | Gopalkrishnan et al. |
| 6,358,907 B1 | 3/2002 | Vitomir |
| 6,372,701 B2 | 4/2002 | Aszman et al. |
| 6,387,865 B1 | 5/2002 | Mondin et al. |
| 6,399,556 B2 | 6/2002 | Smith et al. |
| 6,399,563 B1 | 6/2002 | Durbut et al. |
| 6,407,051 B1 | 6/2002 | Smith et al. |
| 6,425,406 B1 | 7/2002 | Klinkhammer et al. |
| 6,440,924 B1 | 8/2002 | Jeschke et al. |
| 6,486,117 B1 | 11/2002 | Painter et al. |
| 6,491,728 B2 | 12/2002 | Bacon et al. |
| 6,491,933 B2 | 12/2002 | Lorenzi et al. |
| 6,510,561 B1 | 1/2003 | Hammond et al. |
| 6,524,594 B1 | 2/2003 | Santora et al. |
| 6,550,092 B1 | 4/2003 | Brown et al. |
| 6,555,511 B2 | 4/2003 | Renfrow |
| 6,559,116 B1 | 5/2003 | Godfroid et al. |
| 6,605,584 B2 | 8/2003 | Fong et al. |
| 6,634,037 B2 | 10/2003 | Turbett et al. |
| 6,649,580 B2 | 11/2003 | Aszman et al. |
| 6,667,286 B1 | 12/2003 | Dettinger et al. |
| 6,667,287 B2 | 12/2003 | Aszman et al. |
| 6,677,294 B2 | 1/2004 | Shaw et al. |
| 6,680,287 B2 | 1/2004 | Wisniewski et al. |
| 6,683,035 B1 | 1/2004 | Koester et al. |
| 6,696,395 B1 | 2/2004 | Woo et al. |
| 6,701,940 B2 | 3/2004 | Tsibouklis et al. |
| 6,710,024 B2 | 3/2004 | Raether et al. |
| 6,713,441 B1 | 3/2004 | DeSenna et al. |
| 6,716,804 B2 | 4/2004 | Scherubel et al. |
| 6,737,394 B2 | 5/2004 | Shana'a et al. |
| 6,770,607 B2 | 8/2004 | Chen et al. |
| 6,770,613 B2 | 8/2004 | Aouad et al. |

(56) References Cited

U.S. PATENT DOCUMENTS

| | | |
|---|---|---|
| 6,772,450 B1 | 8/2004 | Saylor et al. |
| 6,794,349 B2 | 9/2004 | Hafkamp et al. |
| 6,797,683 B2 | 9/2004 | Shana'a et al. |
| 6,828,290 B1 | 12/2004 | Evers et al. |
| 6,831,052 B2 | 12/2004 | Weuthen et al. |
| 6,835,705 B2 | 12/2004 | Shaukat et al. |
| 6,838,426 B1 | 1/2005 | Zeilinger |
| 6,849,588 B2 | 2/2005 | Elsik et al. |
| 6,905,276 B2 | 6/2005 | Van Buskirk et al. |
| 6,914,075 B2 | 7/2005 | Nakano et al. |
| 6,984,617 B2 | 1/2006 | Holland et al. |
| 7,018,970 B2 | 3/2006 | Hsu et al. |
| 7,048,205 B2 | 5/2006 | MoodyCliffe et al. |
| 7,071,155 B2 | 7/2006 | Griese et al. |
| 7,144,177 B2 | 12/2006 | Van Buskirk et al. |
| 7,192,601 B2 | 3/2007 | Walker |
| 7,193,002 B2 | 3/2007 | Chen |
| 7,276,472 B2 | 10/2007 | Farooq et al. |
| 7,427,170 B2 | 9/2008 | Van Buskirk et al. |
| 7,727,948 B2 | 6/2010 | Mock-Knoblauch et al. |
| 2001/0003738 A1 | 6/2001 | Wise |
| 2001/0035434 A1 | 11/2001 | Both et al. |
| 2001/0044395 A1 | 11/2001 | Aszman et al. |
| 2002/0004469 A1 | 1/2002 | Faber |
| 2002/0010105 A1 | 1/2002 | Bacon et al. |
| 2002/0010430 A1 | 1/2002 | Dragan et al. |
| 2002/0037824 A1 | 3/2002 | Smets et al. |
| 2002/0107165 A1 | 8/2002 | Weuthen et al. |
| 2002/0111280 A1 | 8/2002 | Trage et al. |
| 2002/0115581 A1 | 8/2002 | DuVal et al. |
| 2002/0132746 A1 | 9/2002 | Desenna et al. |
| 2002/0147122 A1 | 10/2002 | Shick et al. |
| 2002/0151449 A1 | 10/2002 | Fox et al. |
| 2003/0008792 A1 | 1/2003 | Shaukat et al. |
| 2003/0022809 A1 | 1/2003 | Weuthen et al. |
| 2003/0032349 A1 | 2/2003 | Gott et al. |
| 2003/0050247 A1 | 3/2003 | Kuhner et al. |
| 2003/0083209 A1 | 5/2003 | MoodyCliffe et al. |
| 2003/0083210 A1 | 5/2003 | Goldberg et al. |
| 2003/0083224 A1 | 5/2003 | Wick et al. |
| 2003/0096726 A1 | 5/2003 | Smith et al. |
| 2003/0109395 A1 | 6/2003 | Neumiller |
| 2003/0109413 A1 | 6/2003 | Geffroy et al. |
| 2003/0119688 A1 | 6/2003 | Rehm et al. |
| 2003/0125220 A1 | 7/2003 | Dykstra et al. |
| 2003/0144167 A1 | 7/2003 | Sivik et al. |
| 2003/0144171 A1 | 7/2003 | Henning et al. |
| 2003/0158079 A1 | 8/2003 | Dykstra et al. |
| 2003/0166496 A1 | 9/2003 | Godfroid et al. |
| 2003/0181348 A1 | 9/2003 | Merz et al. |
| 2003/0195134 A1 | 10/2003 | Vandijk et al. |
| 2003/0207779 A1 | 11/2003 | Wise |
| 2003/0220223 A1 | 11/2003 | Scheuing et al. |
| 2003/0232730 A1 | 12/2003 | Holland et al. |
| 2004/0034911 A1 | 2/2004 | Day |
| 2004/0043911 A1 | 3/2004 | Shaw et al. |
| 2004/0049839 A1 | 3/2004 | MoodyCliffe et al. |
| 2004/0067866 A1 | 4/2004 | Griese et al. |
| 2004/0067869 A1 | 4/2004 | Sivik et al. |
| 2004/0072710 A1 | 4/2004 | McKechnie et al. |
| 2004/0110648 A1 | 6/2004 | Jordan, IV et al. |
| 2004/0120915 A1 | 6/2004 | Yang et al. |
| 2004/0147416 A1 | 7/2004 | Woo et al. |
| 2004/0202503 A1 | 10/2004 | Buskirk et al. |
| 2004/0265261 A1 | 12/2004 | Kohut et al. |
| 2004/0266638 A1 | 12/2004 | Requejo et al. |
| 2005/0008576 A1 | 1/2005 | Makansi |
| 2005/0014668 A1 | 1/2005 | Bariou et al. |
| 2005/0020473 A1 | 1/2005 | Gallotti et al. |
| 2005/0049154 A1 | 3/2005 | Brady |
| 2005/0085405 A1 | 4/2005 | Shaw et al. |
| 2005/0090412 A1 | 4/2005 | Hsu et al. |
| 2005/0167450 A1 | 8/2005 | Lanzendorfer et al. |
| 2005/0189377 A1 | 9/2005 | Lanzendorfer et al. |
| 2005/0197268 A1 | 9/2005 | Buskirk et al. |
| 2005/0239675 A1 | 10/2005 | Makansi |
| 2005/0251944 A1 | 11/2005 | Buskirk et al. |
| 2005/0277568 A1 | 12/2005 | Keenan et al. |
| 2006/0030510 A1 | 2/2006 | Dabholkar et al. |
| 2006/0030511 A1 | 2/2006 | Makins Holland et al. |
| 2006/0058207 A1 | 3/2006 | Shaw et al. |
| 2006/0111262 A1 | 5/2006 | Conzelmann et al. |
| 2006/0166849 A1 | 7/2006 | Kilkenny et al. |
| 2006/0204526 A1 | 9/2006 | Lathrop et al. |
| 2006/0258557 A1 | 11/2006 | Popplewell et al. |
| 2006/0270582 A1 | 11/2006 | Boeckh et al. |
| 2007/0003500 A1 | 1/2007 | Cheung et al. |
| 2007/0041925 A1 | 2/2007 | Picano et al. |
| 2007/0093401 A1 | 4/2007 | Murthy et al. |
| 2007/0160651 A1 | 7/2007 | Mueller et al. |
| 2007/0185005 A1 | 8/2007 | Cornelius et al. |
| 2008/0057020 A1 | 3/2008 | Sarcinelli et al. |
| 2008/0058239 A1 | 3/2008 | Evers et al. |
| 2008/0058240 A1 | 3/2008 | Evers et al. |
| 2008/0058241 A1 | 3/2008 | Sarcinelli et al. |
| 2008/0103066 A1 | 5/2008 | Huang et al. |
| 2008/0171685 A1 | 7/2008 | Cobb et al. |
| 2008/0242583 A1 | 10/2008 | Cornelius et al. |
| 2008/0255017 A1 | 10/2008 | Dettinger et al. |
| 2008/0293612 A1 | 11/2008 | Kellar et al. |
| 2009/0215661 A1 | 8/2009 | Klinkhammer et al. |
| 2010/0093586 A1 | 4/2010 | Klinkhammer et al. |
| 2010/0130399 A1 | 5/2010 | Abbas et al. |
| 2010/0130400 A1 | 5/2010 | Abbas et al. |
| 2010/0162474 A1 | 7/2010 | Abbas et al. |
| 2011/0002871 A1 | 1/2011 | Leipold |
| 2011/0112006 A1 | 5/2011 | Cobb et al. |
| 2011/0142784 A1 | 6/2011 | Leipold et al. |

FOREIGN PATENT DOCUMENTS

| | | |
|---|---|---|
| EP | 1325103 A1 | 7/2003 |
| EP | 1418225 A1 | 5/2004 |
| EP | 1894578 A1 | 3/2008 |
| EP | 1894989 A1 | 3/2008 |
| EP | 1894990 A1 | 3/2008 |
| EP | 1894991 A1 | 3/2008 |
| EP | 1894992 A1 | 3/2008 |
| EP | 1978080 A1 | 10/2008 |
| GB | 2280906 A | 2/1995 |
| GB | 2288186 A | 10/1995 |
| JP | 60-141797 A | 7/1985 |
| WO | 9203532 A1 | 3/1992 |
| WO | 9705232 A1 | 2/1997 |
| WO | 9725408 A1 | 7/1997 |
| WO | 9846712 A1 | 10/1998 |
| WO | 9966017 A1 | 12/1999 |
| WO | 9966021 A1 | 12/1999 |
| WO | 0053718 A1 | 9/2000 |
| WO | 0181519 A1 | 11/2001 |
| WO | 0204591 A1 | 1/2002 |
| WO | 0212431 A1 | 2/2002 |
| WO | 0226925 A1 | 4/2002 |
| WO | 03043906 A1 | 5/2003 |
| WO | 03066797 A1 | 8/2003 |
| WO | 03074095 A1 | 9/2003 |
| WO | 2004024101 A1 | 3/2004 |
| WO | 2004043825 A1 | 5/2004 |
| WO | 2005049783 A1 | 6/2005 |
| WO | 2006056301 A1 | 6/2006 |
| WO | 2006134350 A1 | 12/2006 |
| WO | 2008058853 A1 | 5/2008 |
| WO | 2008068488 A1 | 6/2008 |

CLEANING COMPOSITION THAT PROVIDES RESIDUAL BENEFITS

CROSS REFERENCE TO RELATED APPLICATIONS

This application is a continuation of U.S. Ser. No. 12/461,103 filed Jul. 31, 2009, which is a continuation-in-part of U.S. Ser. No. 12/388,588 filed Feb. 19, 2009, which claims the benefit of U.S. Provisional Application No. 61/064,181, filed Feb. 21, 2008.

REFERENCE REGARDING FEDERALLY SPONSORED RESEARCH OR DEVELOPMENT

Not applicable.

SEQUENTIAL LISTING

Not applicable.

FIELD OF INVENTION

In some embodiments, the invention is directed to a self-adhering composition that may provide residual benefits based on an extended spreading or coating provided by the composition upon exposure to a layer of water. In addition, the composition has improved stability under varying conditions of temperature and humidity, as well as improved self-adhesion to hard surfaces, for example a ceramic surface, such as toilet bowls, glass, windows, doors, shower or bath walls, and the like. Additionally, due to the inclusion of a blend of certain linear primary alcohols or blend of certain ethoxylated linear primary alcohols, a composition as described has improved stability during manufacture and as a finished product.

BACKGROUND OF INVENTION

It is known to hang cleaning and/or disinfecting and/or fragrancing agents in a container under the rim of a toilet bowl by appropriate hanging devices from which the sanitary agents are released upon each flush into the toilet bowl.

While effective, some consumers do not use such devices because of reasons such as the need to remove a used device by hand. For example, consumers may perceive such requirement as unsanitary or generally unappealing. Additionally, only one device may be used at a time in a toilet bowl and such devices tend to release composition locally, resulting in an effect that may be limited by the location and flow of the water.

In addition, consumers may shy away from using conventional under-the-rim toilet bowl hanging devices because such devices may impede the consumer during the course of a regular cleaning. During cleaning with a toilet bowl brush, a hanging device may be easily displaced and then must be put back in place by using the consumers' hands, which may be perceived as unhygienic or unappealing.

Exemplary sanitary agents for dispensing in toilet bowls may be in the form of solid blocks, liquids, and gel form.

U.S. Pat. No. 6,667,286 discloses a sanitary agent in paste or gel form which provides a long-lasting cleaning and/or deodorant-releasing and/or disinfecting effect and which can be applied directly to the surface of a toilet bowl in a simple and hygienic manner. U.S. Pat. App. Pub. No. 2008/0190457 discloses a self-sticking cleansing block that may be applied directly to the surface of a toilet bowl. The present invention provides an improvement to such a sanitary agent by providing greater stability, e.g. longevity in use, as well as improved self-adhesion to hard surfaces, especially ceramic surfaces such as a toilet bowl.

In some embodiments, the present invention provides consumers with the benefit of delivering a composition or active ingredient to a relatively wide area of a toilet bowl or other hard surface. In other nonlimiting embodiments, the present invention provides consumers with the benefit of efficiently delivering a composition or active ingredient to a relative wide area of the toilet bowl or other hard surface. In some embodiments, improved component stability is achieved through the inclusion in the composition of certain blends of linear primary alcohols or blends of ethoxylated linear primary alcohols.

SUMMARY OF THE INVENTION

In a first nonlimiting embodiment, the present invention relates to a composition for use on a hard surface. The composition has: (i) at least 7.5 wt. % of at least one surfactant selected; (ii) from 0 wt. % to about 2.0 wt. % of a blend of linear primary alcohols or a blend of ethoxylated linear primary alcohols, wherein each alcohol of the blends includes a carbon chain containing from 9-17 carbons; (iii) a transport rate factor of less than about 55 seconds; and (iv) an adhesion time of greater than about 8 hours.

In a second nonlimiting embodiment, the present invention relates to a gel composition for use on a hard surface. The composition has: (i) less than 6 wt. % fragrance; (ii) from 0 wt. % to about 2.0 wt. % of a blend of linear primary alcohols or a blend of ethoxylated linear primary alcohols, wherein each alcohol of the blends includes a carbon chain containing from 9-17 carbons; and (iii) a transport rate factor of less than about 55 seconds.

In a third nonlimiting embodiment, the present invention relates to a solid composition for use on a hard surface. The composition has: (i) less than 10 wt. % fragrance; (ii) from 0 wt. % to about 2.0 wt. % of a blend of linear primary alcohols or a blend of ethoxylated linear primary alcohols, wherein each alcohol of the blend includes a carbon chain containing from 9-17 carbons; and (iii) a transport rate factor of less than about 55 seconds.

In a fourth nonlimiting embodiment, the present invention relates to a composition for use on a hard surface. The composition has: (i) at least 7.5 wt. % of at least one surfactant; (ii) from 0 wt. % to about 2.0 wt. % of a blend of linear primary alcohols or a blend of ethoxylated linear primary alcohols wherein each alcohol of the blends includes a carbon chain containing from 9-17 carbons; (iii) less than about 10 wt. % fragrance; and (iv) a transport rate factor of less than about 55 seconds.

BRIEF DESCRIPTION OF THE DRAWINGS

The following detailed description of specific nonlimiting embodiments of the present invention can be best understood when read in conjunction with the following drawings, where like structures are indicated with like reference numerals and in which.

DETAILED DESCRIPTION OF THE INVENTION

Definitions

Figure 1:
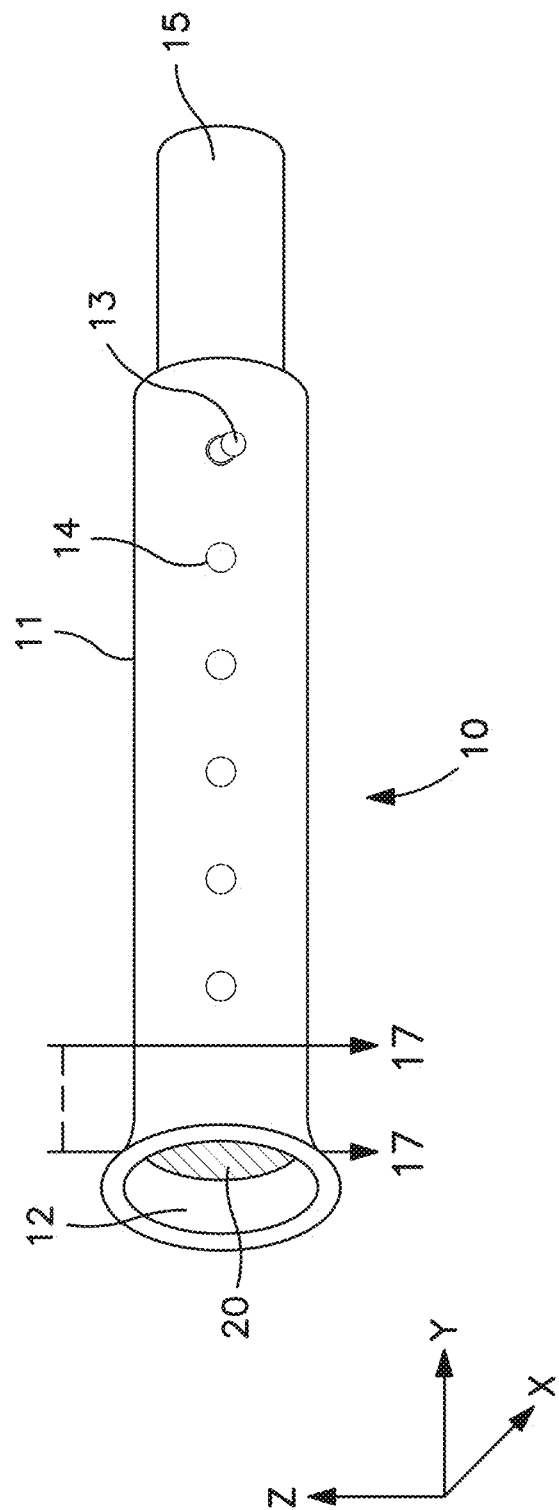
FIG. 1 shows perspective view of an exemplary gel dispensing apparatus according to the present invention.
Figure 2A:
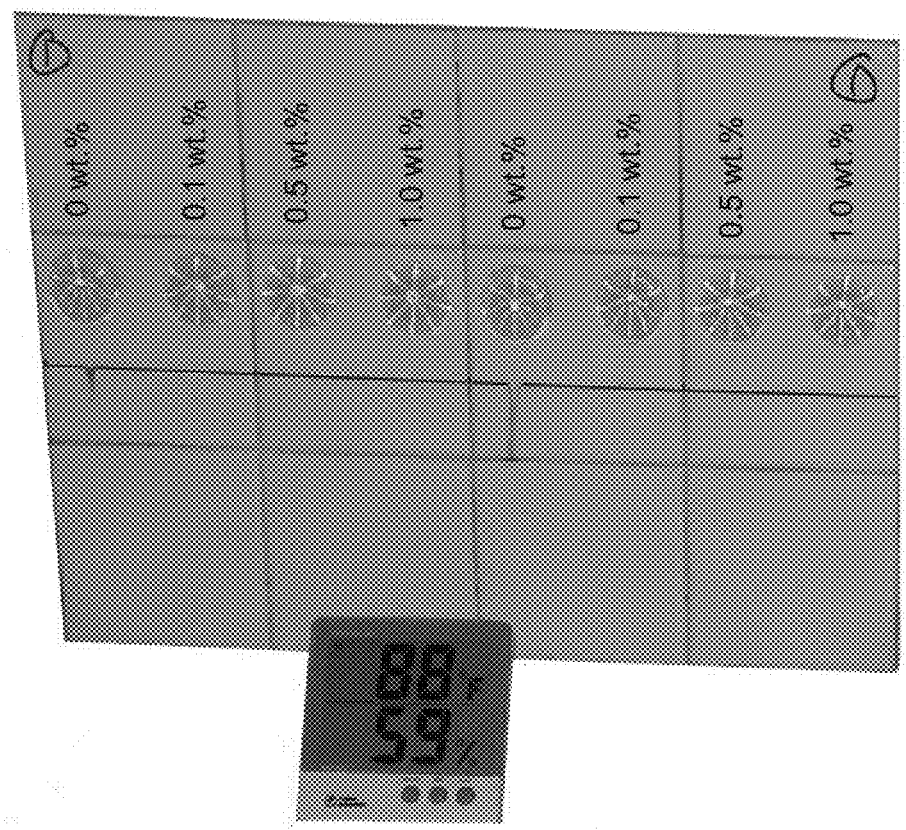
FIGS. 2A-E shows gel compositions having different mineral oil compositions at different times under test conditions as described below.
Figure 2B:
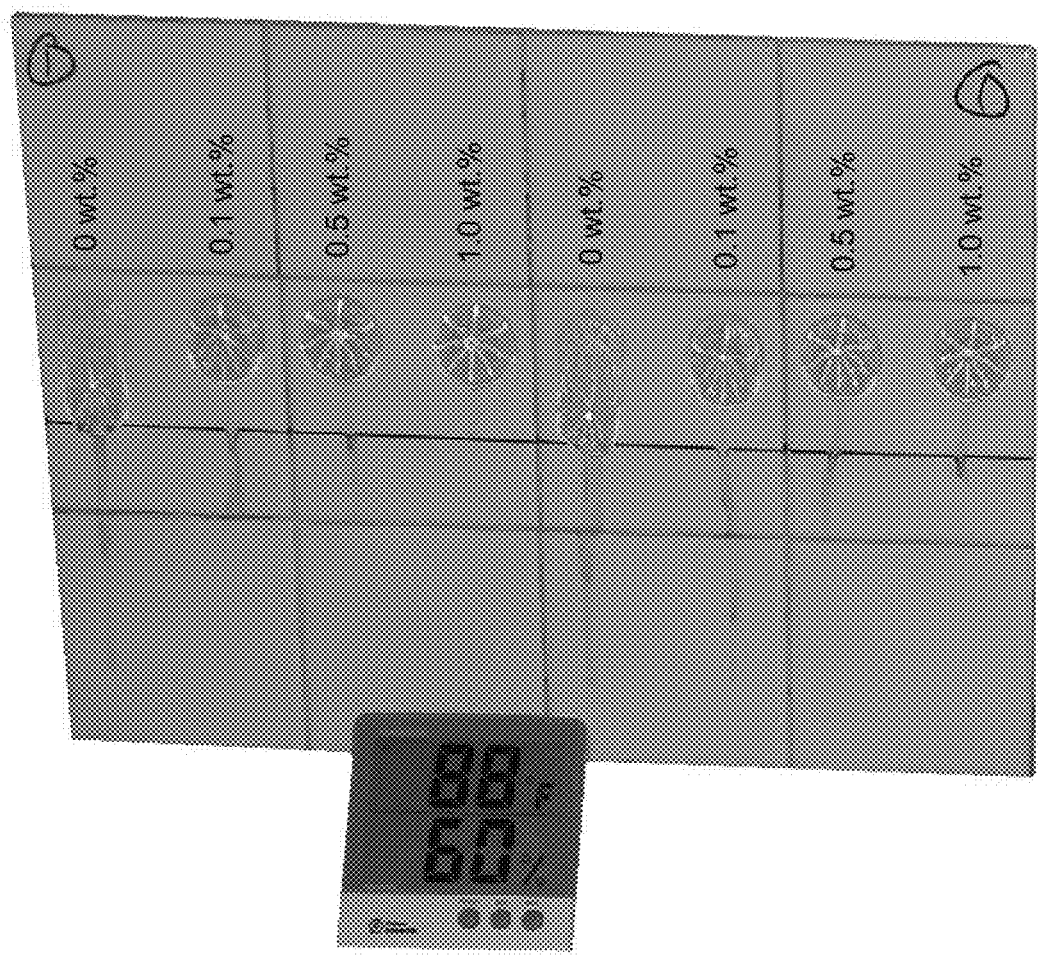
Figure 2C:
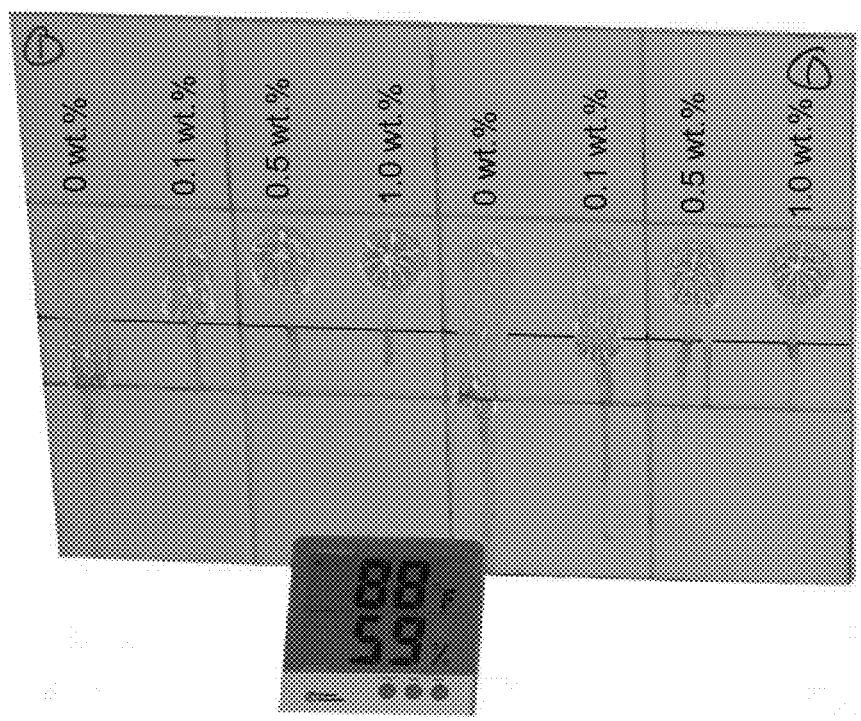
Figure 2D:
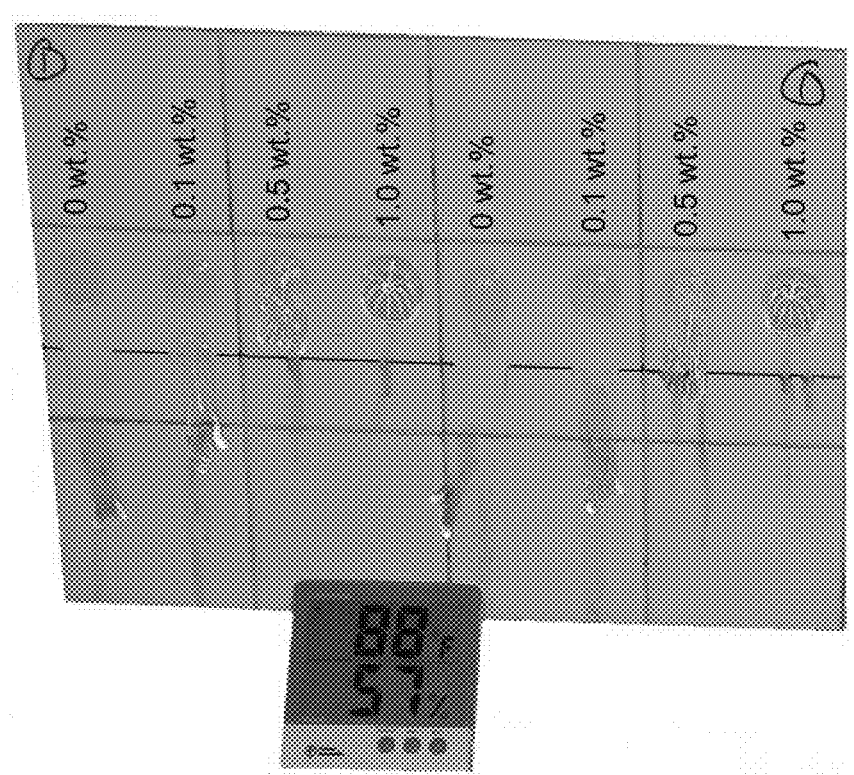
Figure 2E:
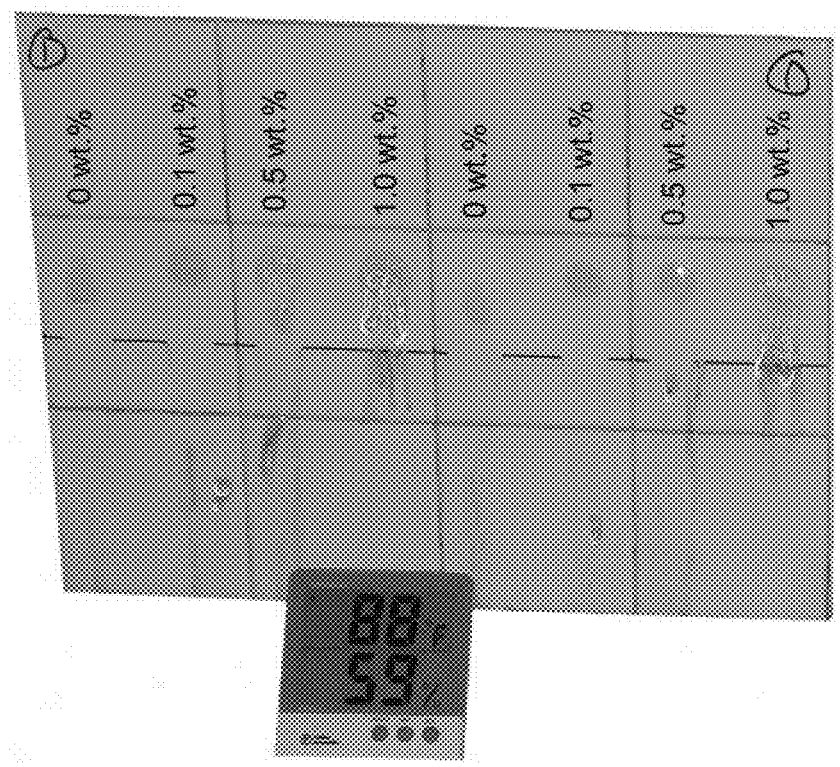

As used herein, "composition" refers to any solid, gel and/or paste substance having more than one component.

As used herein, "self adhesive" refers to the ability of a composition to stick onto a hard surface without the need for a separate adhesive or other support device. In one embodiment, a self adhesive composition does not leave any residue or other substance (i.e., additional adhesive) once the composition is used up.

As used herein, "gel" refers to a disordered solid composed of a liquid with a network of interacting particles or polymers which has a non-zero yield stress.

As used herein, "fragrance" refers to any perfume, odor-eliminator, odor masking agent, the like, and combinations thereof. In some embodiments, a fragrance is any substance which may have an effect on a consumer, or user's, olfactory senses.

As used herein, "wt. %" refers to the weight percentage of actual active ingredient in the total formula. For example, an off-the-shelf composition of Formula X may only contain 70% active ingredient X. Thus, 10 g. of the off-the-shelf composition only contains 7 g. of X. If 10 g. of the off-the-shelf composition is added to 90 g. of other ingredients, the wt. % of X in the final formula is thus only 7%.

As used herein, "hard surface" refers to any porous and/or non-porous surface. In one embodiment, a hard surface may be selected from the group consisting of: ceramic, glass, metal, polymer, stone, and combinations thereof. In another embodiment, a hard surface does not include silicon wafers and/or other semiconductor materials. Nonlimiting examples of ceramic surfaces include: toilet bowl, sink, shower, tile, the like, and combinations thereof. A nonlimiting example of a glass surfaces includes: window and the like. Nonlimiting examples of metal surfaces include: drain pipe, sink, automobiles, the like, and combinations thereof. Nonlimiting examples of a polymeric surface includes: PVC piping, fiberglass, acrylic, Corian®, the like, and combinations thereof. A nonlimiting example of a stone hard surface includes: granite, marble, and the like.

A hard surface may be any shape, size, or have any orientation that is suitable for its desired purpose. In one nonlimiting example, a hard surface may be a window which may be oriented in a vertical configuration. In another nonlimiting example, a hard surface may be the surface of a curved surface, such as a ceramic toilet bowl. In yet another nonlimiting example, a hard surface may be the inside of a pipe, which has vertical and horizontal elements, and also may have curved elements. It is thought that the shape, size and/or orientation of the hard surface will not affect the compositions of the present invention because of the unexpectedly strong transport properties of the compositions under the conditions described infra.

As used herein, "surfactant" refers to any agent that lowers the surface tension of a liquid, for example water. Exemplary surfactants which may be suitable for use with the present invention are described infra. In one embodiment, surfactants may be selected from the group consisting of anionic, non-ionic, cationic, amphoteric, zwitterionic, and combinations thereof. In one embodiment, the present invention does not comprise cationic surfactants. In other nonlimiting embodiments, the surfactant may be a super-wetter. One of skill in the art will appreciate that in some embodiments, a substance which may be used as an adhesion promoter may also be a surfactant.

In use, the composition of the invention may be applied directly on the hard surface to be treated, e.g. cleaned, such as a toilet bowl, shower or bath enclosure, drain, window, or the like, and self-adheres thereto, including through a plurality of flows of water passing over the self-adhering composition and surface, e.g. flushes, showers, rinses or the like. Each time water flows over the composition, a portion of the composition is released into the water that flows over the composition. The portion of the composition released onto the water covered surface provides a continuous wet film to the surface to in turn provide for immediate and long term cleaning and/or disinfecting and/or fragrancing or other surface treatment depending on the active agent(s) present in the composition. It is thought that the composition, and thus the active agents of the composition, may spread out from or are delivered from the initial composition placement in direct contact with the surface to coat continuously an extended area on the surface. The wet film acts as a coating and emanates from the self-adhering composition in all directions, i.e., 360°, from the composition, which includes in a direction against the flow of the rinse water. Motions of the surface of a liquid are coupled with those of the subsurface fluid or fluids, so that movements of the liquid normally produce stresses in the surface and vice versa. The mechanism for the movement of the gel and/or the active ingredients is discussed in greater detail infra.

Surprisingly, it is observed that the nonlimiting exemplary compositions of the present invention provide for a more rapid and extended self-spreading. Without wishing to be limited by theory, it is thought that the self-spreading effect may be modified through the addition of specific surfactants to the composition. Nonlimiting examples of factors which are thought to affect the speed and distance of the self spreading include: the amount of surfactant present, the type of surfactant present, the combination of surfactants present, the amount of spreading of the surfactant over the water flow, the ability of the surfactant to adsorb at the liquid/air interface, and the surface energy of the treated surface. It is thought that the surfactant of the composition serves to push other molecules, e.g. compounds, around so as to deliver these compounds to other parts of the surface. Compounds desirable for extended delivery over a treated surface are active agents, e.g. agents capable of activity as opposed to being inert or static. Nonlimiting examples of active agents, or active ingredients, that may be used include: cleaning compounds, germicides, antimicrobials, bleaches, fragrances, surface modifiers, stain preventers (such as a chelator) the like, and combinations thereof. The composition is especially useful in treating the surface of a toilet bowl since it allows for delivery and retention of a desired active agent on a surface above the water line in the bowl as well as below the water line.

In some embodiments, the composition can be applied directly to a surface using any suitable applicator device, such as a pump or syringe-type device, manual, pressurized, or mechanized, aerosol, or sprayer. The consumer may activate the applicator for application of the composition directly to a surface without the need to touch the surface. In the case of a toilet bowl surface, this provides for a hygienic and easily accessible method of application. The amount and location(s) of the composition may be chosen by the user, e.g. one or more dollops or drops of composition, or one or more lines of composition. The composition self-adheres to a hard surface to which it is applied, such as the ceramic side wall of a toilet bowl or shower wall. A surprising and unique feature not provided by conventional devices is that the composition is delivered to surfaces located above the site of application of the composition to the surface.

Composition

In one embodiment, the composition has a gel or gel-like consistency. In the described embodiment, the composition is, thus, firm but not rigid as a solid. In an alternative embodiment, the composition is a solid. In still another embodiment, the composition is a malleable solid.

The improved adhesion obtained by the composition of the invention allows application on a vertical surface without becoming detached through a plurality of streams of rinse water and the gradual washing away of a portion of the composition over time to provide the desired cleaning and/or disinfecting and/or fragrance or other treatment action. Once the composition is completely washed away, nothing remains for removal and more composition is simply applied.

In some embodiments, the composition may include an adhesion promoter which causes a bond with water and gives the composition a dimensional stability even under the action of rinse water; at least one nonionic surfactant (which may serve all or in part as the adhesion promoter), preferably an ethoxylated alcohol; at least one anionic surfactant, preferably an alkali metal alkyl ether sulfate or sulfonate; mineral oil; a blend of linear primary alcohols or a blend of ethoxylated linear primary alcohols, wherein each alcohol of the blends includes a carbon chain containing 9 to 17 carbons (also referred to herein for convenience as the "linear C9-C17 primary alcohol blend" or "ethoxylated linear C9-C17 primary alcohol blend", respectively); water; and optionally at least one solvent. More particularly, the hydrophilic polymer holds the composition to the surface to enhance the maintenance and thereby extend the times of spreading and, thus, delivery of active agents for treatment of the surface and/or surrounding environment. In some embodiments, the composition may also include a superwetter compound to enhance the spreading of the wet film. The composition displays extended durability without the necessity of an exterior hanging device or holder thereby only requiring a new application of the composition to the surface after a long lapse of time and no need to remove any device. The linear C9-C17 primary alcohol blend and ethoxylated linear C9-C17 primary alcohol blend each serve to lower the gel temperature of the composition during processing which allows the composition to be processed at a lower temperature which reduces degradation or the chance of degradation of composition components. The inclusion of the linear C9-C17 primary alcohol blend or ethoxylated linear C9-C17 primary alcohol blend each, therefore, provide for more stable components and, thus, more stable product. A key formulating parameter for the composition of the invention is adhesion. Generally, to improve product performance, the adhesive property of the composition is increased. Upon increase in adhesion, however, the gel point of the composition also increases. It is desired for optimum product performance to keep the gel point balanced minimizing the processing temperature while maintaining the composition's gel structure under and during shipping, storage and use conditions. This is obtained through the inclusion of the linear C9-C17 primary alcohol blend or the ethoxylated linear C9-C17 primary alcohol blend, which serve to reduce or suppress the gel point to a desired value with minimal effect on adhesion, force to actuate and maximum gel viscosity.

In some nonlimiting examples, there are a number of components of the present invention composition that are suitable for treating hard surfaces. In one embodiment, the composition comprises an adhesion promoter present in an amount of from about 20 wt. % to about 80 wt. %. In another embodiment, the composition comprises an adhesion promoter in the amount of from about 20 wt. % to about 60 wt. %. In another embodiment, the composition comprises an adhesion promoter in the amount of from about 40 wt. % to about 60 wt. %. In an alternative embodiment, the composition comprises an adhesion promoter in the amount of from about 20 wt. % to about 30 wt. %.

In another embodiment, the composition comprises at least one surfactant in an amount of greater than 7.5 wt. %. In another embodiment, the composition comprises at least one surfactant in an amount of from about 7.5 wt. % to about 20 wt. %. Surprisingly, it is discovered that providing an optimal amount of surfactant, in particular anionic surfactant, provides the product with a particularly strong "foaming" characteristic that greatly pleases consumers.

In one embodiment, the composition comprises a nonpolar hydrocarbon such as mineral oil in an amount of less than about 5 wt. %. In another embodiment, the composition comprises mineral oil in an amount of from greater than zero wt. % to about 5 wt. %. In another embodiment, the composition comprises mineral oil in an amount of from about 0.5 wt. % to about 3 wt. %.

In one embodiment of the composition, the composition comprises a linear C9-C17 primary alcohol blend or an ethoxylated linear C9-C17 primary alcohol blend present in an amount greater than 0 wt. % to about 2.0 wt. %. In another embodiment, the composition comprises a linear C9-C17 primary alcohol blend or an ethoxylated linear C9-C17 primary alcohol blend present in an amount of from about 0.2 wt. % to about 1.0 wt. %. In another embodiment, the composition comprises a linear C9-C17 primary alcohol blend or an ethoxylated linear C9-C17 primary alcohol blend present in an amount of about 0.4 wt. % to about 0.8 wt. %. In an alternative embodiment, the composition comprises about 0.6 wt. % of a linear C9-C17 primary alcohol blend or an ethoxylated linear C9-C17 primary alcohol blend. Surprisingly, it has been found that the inclusion of a linear C9-C17 primary alcohol blend or an ethoxylated linear C9-C17 primary alcohol blend serves to lower the gel temperature of the composition approximately 2° C. for each 0.1 wt. % of the non-ethoxylated or ethoxylated alcohol blend included in the composition which allows the product to be processed at a lower temperature, which during production and subsequently, serves to reduce component and, thus, product degradation. This is particularly advantageous since some of the raw materials or components added during processing should not be processed at a temperature above 45° C. The inclusion of the linear C9-C17 primary alcohol blend or an ethoxylated linear C9-C17 primary alcohol blend provides for enhanced stability of the composition.

In some embodiments, the compositions may be brought to 100 wt. % using any suitable material for the intended application. One of skill in the art will appreciate that this may include, but not be limited to, a balance of water, surface modifiers, germicides, bleaches, cleaners, foamers, the like, and combinations thereof.

Optionally, the compositions of the present invention may further comprise at least one solvent in an amount of from 0 wt. % to about 15 wt. % and the composition may further comprise at least one fragrance in an amount of from 0 wt. % to about 15 wt. %. Additionally, the composition may optionally include a hydrophilic polymer in an amount from 0 wt. % to about 5 wt. % to amplify transport effects of the composition. In one embodiment, "solvent" does not include water.

A further optional component is a superwetter. Without wishing to be limited by theory, it is thought that a superwetter may enhance the wet film provided in use of the composition. Superwetters, as may be used in the present invention composition, are described in greater detail infra. In other nonlimiting embodiments, additional optional components include conventional adjuvants, such as a preservative, colorant, foam stabilizer, antimicrobial, germicide, or the like, present in an effective amount.

Exemplary components suitable for use as an adhesion promoter may have long or long-chained molecules, for the most part linear, that are at least in part hydrophilic and thus include at least a hydrophilic residual or a hydrophilic group so as to provide interaction with water molecules. Preferably, the adhesion promoter has unbranched molecules to form a desired network-like structure to form adhesion-promoting molecules. The adhesion promoter may be totally hydrophilic or partly hydrophilic, partly hydrophobic.

Exemplary pure adhesion hydrophilic promoters suitable for use in the present invention include, for example: polyethylene glycol, cellulose, especially sodium carboxymethyl cellulose, hydroxyethyl cellulose, hydroxypropyl cellulose, or polysaccharides such as xanthan gum, agar, gellan gum, acacia gum, carob bean flour, guar gum or starch. Polysaccharides can form networks with the necessary solidity and a sufficient stickiness in concentrations of from 0 wt. % to about 10 wt. %; from 0 wt. % to about 5 wt. %; and from about 1 wt. % to about 2 wt. %.

The adhesion-promoting molecules can be synthetic or natural polymers, for instance, polyacrylates, polysaccharides, polyvinyl alcohols, or polyvinyl pyrrolidones. It is also possible to use alginates, diurethanes, gelatines, pectines, oleyl amines, alkyl dimethyl amine oxides, or alkyl ether sulfates.

Organic molecules with a hydrophilic and hydrophobic end may also be used as adhesion promoters. As hydrophilic residuals, for example, polyalkoxy groups, preferably polyethoxy, polypropoxy, or polybutyoxy or mixed polyalkoxy groups such as, for example, poly(ethoxypropoxy) groups can be used. Especially preferred for use as a hydrophilic end, for example, is a polyethoxy residual including from 15 to 55 ethoxy groups, preferably from 25 to 45 and more preferably from 30 to 40 ethoxy groups.

In some embodiments, anionic groups, for example, sulfonates, carbonates, or sulfates, can be used as hydrophilic ends. In other embodiments, stearates, especially sodium or potassium stearate, are suitable as adhesion promoters.

In embodiments wherein the adhesion-promoting molecules also have a hydrophobic end, straight-chained alkyl residuals are preferred for the hydrophobic residual, whereby in particular even-numbered alkyl residuals are preferred because of the better biological degradability.

Without wishing to be limited by theory, it is thought that to obtain the desired network formation of the adhesion-promoting molecules, the molecules should be unbranched.

If alkyl residuals are chosen as hydrophobic residuals, alkyl residuals with at least 12 carbon atoms are preferred. More preferred are alkyl chain lengths of from 16 to 30 carbon atoms, most preferred is from 20 to 22 carbon atoms.

Exemplary adhesion promoters are polyalkoxyalkanes, preferably a mixture of $C_{20}$ to $C_{22}$ alkyl ethoxylate with from 18 to 50 ethylene oxide groups (EO), preferably from about 25 to about 35 EO, and also sodium dodecylbenzene sulfonate. With a reduction of the number of alkoxy groups the adhesion promoter becomes more lipophilic, whereby, for example, the solubility of perfume and thus the intensity of the fragrance can be raised.

Molecules that generally act like thickeners in aqueous systems, for example, hydrophilic substances, can also be used as adhesion promoters.

Without wishing to be limited by theory, it is thought that the concentration of the adhesion promoter to be used depends on its hydrophilicity and its power to form a network. When using polysaccharides, for example, concentrations from about 1 wt. % to about 2 wt. % of the adhesion promoter can be sufficient, whereas in embodiments comprising polyalkoxyalkanes the concentrations may be from about 10 wt %. to about 40 wt. %; in another embodiment from about 15 wt. % to about 35 wt. %; and in another embodiment still from about 20 wt. % to about 30 wt. %.

Also without wishing to be limited by theory, it is thought that in order to produce the desired number of adhering sites with the adhesion-promoting molecules through the absorption of water, the composition may contain at least about 25% by weight water, and optionally additional solvent. In one embodiment, the composition comprises water from about 40 wt. % to about 65 wt. %. One of skill in the art will appreciate that the amount of water that is to be used is dependent on, among other things, the adhesion promoter used and the amount of adjuvants also in the formula.

Exemplary anionic surfactants suitable for use include alkali metal $C_6$-$C_{18}$ alkyl ether sulfates, e.g. sodium lauryl ether sulfate; α-olefin sulfonates or methyl taurides. Other suitable anionic surfactants include alkali metal salts of alkyl, alkenyl and alkylaryl sulfates and sulfonates. Some such anionic surfactants have the general formula $RSO_4M$ or $RSO_3M$, where R may be an alkyl or alkenyl group of about 8 to about 20 carbon atoms, or an alkylaryl group, the alkyl portion of which may be a straight- or branched-chain alkyl group of about 9 to about 15 carbon atoms, the aryl portion of which may be phenyl or a derivative thereof, and M may be an alkali metal (e.g., ammonium, sodium, potassium or lithium).

Exemplary nonionic surfactants suitable for use include $C_{20}$-$C_{22}$ alkyl ethoxylate with 18 to 50 ethylene oxide groups (EO). In another embodiment, $C_{20}$-$C_{22}$ alkyl ethoxylate comprise 25 to 35 ethylene oxide groups, preferably as an adhesion promoter and nonionic surfactant.

Additional nonlimiting examples of other nonionic surfactants suitable for use include alkylpolyglycosides such as those available under the trade name GLUCOPON from Henkel, Cincinnati, Ohio, USA. The alkylpolyglycosides have the following formula: RO—(R'O)$_x$—$Z_n$ where R is a monovalent alkyl radical containing 8 to 20 carbon atoms (the alkyl group may be straight or branched, saturated or unsaturated), O is an oxygen atom, R' is a divalent alkyl radical containing 2 to 4 carbon atoms, preferably ethylene or propylene, x is a number having an average value of 0 to 12, Z is a reducing saccharide moiety containing 5 or 6 carbon atoms, preferably a glucose, galactose, glucosyl, or galactosyl residue, and n is a number having an average value of about 0.1 to 10. For a detailed discussion of various alkyl glycosides see U.S. Statutory Invention Registration H468 and U.S. Pat. No. 4,565,647, which are incorporated herein by reference. Some exemplary GLUCOPONS are as follows (where Z is a glucose moiety and x=0) in Table A.

TABLE A

Exemplary Glucopons

| Product | N | R (# carbon atoms) |
|---|---|---|
| 425N | 2.5 | 8-14 |
| 425LF | 2.5 | 8-14 (10 w/w % star-shaped alcohol added) |
| 220UP | 2.5 | 8-10 |
| 225DK | 2.7 | 8-10 |
| 600UP | 2.4 | 12-14 |
| 215CSUP | 2.5 | 8-10 |

Other nonlimiting examples of nonionic surfactants suitable for use include alcohol ethoxylates such as those available under the trade name LUTENSOL from BASF, Ludwigshafen, Germany. These surfactants have the general formula $C_{13}H_{25}/C_{15}H_{27}$—$(OC_2H_4)_n$—OH (the alkyl group being a mixture of $C_{13}/C_{15}$). Especially preferred are LUTENSOL AO3 (n=3), AO8 (n=8), and AO10 (n=10). Other alcohol ethoxylates include secondary alkanols condensed with ($OC_2H_4$) such as TERGITOL 15-S-12, a $C_{11}$-$C_{15}$ secondary alkanol condensed with 12 ($OC_2H_4$) available from Dow Surfactants. Another example of a nonionic surfactant suitable for use is polyoxyethylene (4) lauryl ether. Amine oxides are also suitable.

At least one solvent can be present in the composition to assist in blending of surfactants and other liquids. The solvent is present in an amount of from about 0 wt. % to about 15 wt. %, preferably from about 1 wt. % to about 12 wt. %, and more preferably in an amount from about 5 wt. % to about 10 wt. %. Examples of solvents suitable for use are aliphatic alcohols of up to 8 carbon atoms; alkylene glycols of up to 6 carbon atoms; polyalkylene glycols having up to 6 carbon atoms per alkylene group; mono- or dialkyl ethers of alkylene glycols or polyalkylene glycols having up to 6 carbon atoms per glycol group and up to 6 carbon atoms in each alkyl group; and mono- or diesters of alkylene glycols or polyalkylene glycols having up to 6 carbon atoms per glycol group and up to 6 carbon atoms in each ester group. Specific examples of solvents include t-butanol, t-pentyl alcohol; 2,3-dimethyl-2-butanol, benzyl alcohol or 2-phenyl ethanol, ethylene glycol, propylene glycol, dipropylene glycol, propylene glycol mono-n-butyl ether, dipropylene glycol mono-n-butyl ether, propylene glycol mono-n-propyl ether, dipropylene glycol mono-n-propyl ether, diethylene glycol mono-n-butyl ether, diethylene glycol monomethyl ether, dipropylene glycol monomethyl ether, triethylene glycol, propylene glycol monoacetate, glycerin, ethanol, isopropanol, and dipropylene glycol monoacetate. One preferred solvent is polyethylene glycol.

It is thought that the inclusion of a non-polar hydrocarbon, such as mineral oil, may serve to achieve increased stability and self-adherence to a hard surface, especially a ceramic surface. The mineral oil is present in an amount of greater than 0% by weight to about 5% by weight, based on the total weight of the composition. In one embodiment, mineral oil is present in an amount of from about 0.5% wt. % to about 3.5 wt. %. In another embodiment, mineral oil is present in an amount of from about 0.5 wt. % to about 2 wt. %. The amount of mineral oil to be included will depend on the adhesion performance of the balance of the formula. Without wishing to be limited by theory, it is thought that as the amount of mineral oil is increased, the adhesion is also increased.

Although it provides benefits when used in the composition, it is also thought that the inclusion of the mineral oil in higher amounts without decreasing the amount of surfactant and/or thickener and/or adhesion promoters will result in the composition being thickened to a degree which makes processing of the composition during manufacture and use difficult because the firmness of the composition makes it difficult to process. In manufacture, the processing can be carried out under increased temperatures, but such also increases the cost of manufacture and creates other difficulties due to the increased temperature level.

The inclusion in the composition of the invention of a blend of linear primary alcohols or a blend of ethoxylated linear C9-C17 primary alcohols, wherein each alcohol of the blend includes a carbon chain length containing 9 to 17 carbons, is beneficial in that such has been found to lower the gel temperature about 2° C. for each 0.1 wt. % of the linear C9-C17 primary alcohol blend or the blend of ethoxylated linear C9-C17 primary alcohols present in the composition. The inclusion of the linear C9-C17 primary alcohol blend or the blend of ethoxylated linear C9-C17 primary alcohols allows the cleaning product to be produced at a lower temperature which reduces degradation or the chance of degradation of at least some components of the composition which improves stability of the components and, therefore, also the composition. A product with improved cleaning properties due to the enhanced stability of the product components is thereby obtained.

The lowering of the gel temperature by the inclusion of the linear C9-C17 primary alcohol blend or the ethoxylated linear C9-C-17 primary alcohol blend is beneficial since some of the raw materials of the components forming the cleaning composition should not be processed at a temperature above 45° C. Lowering of the gel temperature during processing, thus, reduces any degradation which occurs to such materials during processing resulting in the full component amount and properties thereof being present in the composition produced. This necessarily also provides a more cost-efficient product since higher amounts of these components do not have to be utilized to account for any degradation which would otherwise occur. The inclusion of the alcohol blend or ethoxylated alcohol blend allow for improved adhesion to improve product performance by keeping the gel point of the composition suppressed to minimize the composition processing temperature while maintaining the desired gel structure under shipping, storage and use conditions. The blends described herein serve to reduce the gel point to a desired value with minimal effect on the properties of adhesion, force to actuate and maximum gel viscosity.

Nonlimiting examples of linear C9-C17 primary alcohol blends suitable for use in the present invention are blends including C12 and C13 alcohols, C9 to C11 alcohols, C12 to C15 alcohols, C14 and C15 alcohols, C11-C13-C15 alcohols, C16 and C17 alcohols, and C10 to C12 alcohols; and the ethoxylates of these blends. Such alcohols are commercially available from the Shell Company and are sold under the trademark NEODOL. Examples of the linear C9-C17 primary alcohol blends include NEODOL 23, NEODOL 91, NEODOL 25, NEODOL 45, NEODOL 135, and NEODOL 67 and NEODOL 1. The generic formula for the alcohols of the blend is $C_nH_{(2n+1)}OH$ wherein n=9-17.

NEODOL ethoxylates suitable for use retain the same description of the parent alcohol followed by a number indicating the average moles of ethylene oxide added, and include, for example, NEODOL 23-1, NEODOL 23-3, NEODOL 23-6.5, NEODOL 23-2, NEODOL 91-8, NEODOL 91-2.5, NEODOL 91-5, NEODOL 91-6, NEODOL 25-2.5, NEODOL 25-3, NEODOL 25-7, NEODOL 25-9, NEODOL 25-5, NEODOL 25-1.3, NEODOL 45-4, NEODOL 45-7, NEODOL 45-6.8 and NEODOL 1-9.

The linear C9-C17 primary alcohol blends, or ethoxylated blends thereof, are present in an amount of greater than 0 wt. % to about 2.0 wt. %, preferably about 0.2 wt. % to about 1.0 wt. %, and more preferably about 0.4 wt. % to about 0.8 wt. %.

A preferred example of a linear C9-C17 primary alcohol blend suitable for use in the present invention is a blend of C12 and C13 primary alcohols, such as sold under the name NEODOL 23. Typical properties of NEODOL 23 are as follows:

| Property | Value |
| --- | --- |
| C11 and lower alcohols | <1% m/m |
| C12 alcohol | 41% m/m |
| C13 alcohol | 58% m/m |
| C14 and higher alcohols | <1% m/m |
| Normality | 75 min % m/m |
| Hydroxyl number | 285-294 mg KOH/g |
| Molecular mass | 191-197 g/mol |

The C12-C13 primary alcohol blend is preferably used in an amount of about 0.2 wt. % to about 0.8 wt. %.

Typical properties for other primary alcohol blends suitable for use in the present invention are set forth below.

(1) NEODOL 25—Typical Properties

| Property | Value |
| --- | --- |
| C11 and lower alcohols | <1% m/m |
| C12 alcohol | 21% m/m |
| C13 alcohol | 29% m/m |
| C14 alcohol | 25% m/m |
| C15 alcohol | 25% m/m |
| C16 and higher alcohols | <1% m/m |
| Normality | 75 min % m/m |
| Hydroxyl number | 267-276 mg KOH/g |
| Molecular mass | 203-210 g/mol |

(2) NEODOL 45—Typical Properties

| Property | Value |
| --- | --- |
| C13 and lower alcohols | 1% m/m |
| C14 alcohol | 49% m/m |
| C15 alcohol | 50% m/m |
| C16 and higher alcohols | <1% m/m |
| Normality | 75 min % m/m |
| Hydroxyl number | 250-257 mg KOH/g |
| Molecular mass | 218-224 g/mol |

(3) NEODOL 91—Typical Properties

| Property | Value |
| --- | --- |
| C8 and lower alcohols | <1% m/m |
| C9 alcohol | 18% m/m |
| C10 alcohol | 42% m/m |
| C11 alcohol | 38% m/m |
| C12 and higher alcohols | 1% m/m |
| Normality | 75 min % m/m |
| Hydroxyl number | 342-355 mg KOH/g |
| Molecular mass | 158-164 g/mol |

(4) NEODOL 67—Typical Properties

| Property | Value |
| --- | --- |
| C14 and lower alcohols | <0.5% m/m |
| C15 alcohol | 5% m/m |
| C16 alcohol | 31% m/m |
| C17 alcohol | 54% m/m |
| C18 alcohol | 7% m/m |
| C19 alcohol | 2% m/m |
| C20 and higher alcohols | <0.2% m/m |
| Normality | 5.0 max % m/m |
| Hydroxyl number | 220-230 mg KOH/g |
| Molecular mass | 244-255 g/mol |

(5) NEODOL 135—Typical Properties

| Property | Value |
| --- | --- |
| C10 and lower alcohols | <0.5% m/m |
| C11 alcohol | 12% m/m |
| C12 alcohol | 1.5% m/m |
| C13 alcohol | 42% m/m |
| C14 alcohol | 1.5% m/m |
| C15 alcohol | 42% m/m |
| C16 and higher alcohols | <0.5% m/m |
| Normality | 75 min % m/m |
| Hydroxyl number | 267-276 mg KOH/g |
| Molecular mass | 203-210 g/mol |

(6) NEODOL 1—Typical Properties

| Property | Value |
| --- | --- |
| C10 and lower alcohols | 0.5% m/m |
| C11 alcohol | 98.5% m/m |
| C12 and higher alcohols | 1% m/m |
| Normality | 75 min % m/m |
| Hydroxyl number | 323-327 mg KOH/g |
| Molecular mass | 172-173 g/mol |

Examples of NEODOL ethoxylates based on certain of the above linear C9-C17 primary alcohol blends, which are suitable for use in the invention, are described below as to certain properties. The average moles of ethylene oxide (EO) present are per mole of alcohol.

(1) NEODOL 23-1—Typical Properties (Average 1 Mole EO)

| Property | Value |
| --- | --- |
| Polyethylene Glycol | 1.0 max % m/m |
| EO/Alcohol ratio | 0.9-1.0 mol/mol |
| Hydroxyl number | 231-241 mg KOH/g |
| Molecular mass | 233-243 g/mol |

(2) NEODOL 23-2—Typical Properties (Average 2 Moles EO)

| Property | Value |
| --- | --- |
| Polyethylene Glycol | 1.0 max % m/m |
| EO/Alcohol ratio | 1.8-2.2 mol/mol |
| Hydroxyl number | 194-204 mg KOH/g |
| Molecular mass | 275-289 g/mol |

(3) NEODOL 23-3—Typical Properties (Average 3 Moles EO)

| Property | Value |
| --- | --- |
| Polyethylene Glycol | 1.0 max % m/m |
| EO/Alcohol ratio | 2.8-3.2 mol/mol |
| Hydroxyl number | 167-177 mg KOH/g |
| Molecular mass | 317-336 g/mol |

(4) NEODOL 23-6.5—Typical Properties (Average 6.5 Moles EO)

| Property | Value |
| --- | --- |
| Polyethylene Glycol | 2 max % m/m |
| EO/Alcohol ratio | 6.0-7.0 mol/mol |
| Hydroxyl number | 112-122 mg KOH/g |
| Molecular mass | 460-501 g/mol |

(5) NEODOL 91-2.5—Typical Properties (Average 2.5 Moles EO)

| Property | Value |
| --- | --- |
| Polyethylene Glycol | 1.0 max % m/m |
| EO/Alcohol ratio | 2.4-2.6 mol/mol |
| Hydroxyl number | 203-213 mg KOH/g |
| Molecular mass | 263-276 g/mol |

(6) NEODOL 91-5—Typical Properties (Average 5 Moles EO)

| Property | Value |
| --- | --- |
| Polyethylene Glycol | 2 max % m/m |
| EO/Alcohol ratio | 4.7-5.3 mol/mol |
| Hydroxyl number | 143-153 mg KOH/g |
| Molecular mass | 367-392 g/mol |

(7) NEODOL 91-6—Typical Properties (Average 6 Moles EO)

| Property | Value |
| --- | --- |
| Polyethylene Glycol | 2 max % m/m |
| EO/Alcohol ratio | 5.7-6.4 mol/mol |
| Hydroxyl number | 127-137 mg KOH/g |
| Molecular mass | 410-442 g/mol |

(8) NEODOL 91-8—Typical Properties (Average 8 Moles EO)

| Property | Value |
| --- | --- |
| Polyethylene Glycol | 2.0 max % m/m |
| EO/Alcohol ratio | 7.4-8.3 mol/mol |
| Hydroxyl number | 105-115 mg KOH/g |
| Molecular mass | 488-534 g/mol |

(9) NEODOL 25-1.3—Typical Properties (Average 1.3 Moles EO)

| Property | Value |
| --- | --- |
| Polyethylene Glycol | 1.0 max % m/m |
| EO/Alcohol ratio | 1.1-1.4 mol/mol |
| Hydroxyl number | 209-219 mg KOH/g |
| Molecular mass | 256-268 g/mol |

(10) NEODOL 25-2.5—Typical Properties (Average 2.5 Moles EO)

| Property | Value |
| --- | --- |
| Polyethylene Glycol | 1 max % m/m |
| EO/Alcohol ratio | 2.3-2.7 mol/mol |
| Hydroxyl number | 172-182 mg KOH/g |
| Molecular mass | 308-326 g/mol |

(11) NEODOL 25-3—Typical Properties (Average 3 Moles EO)

| Property | Value |
| --- | --- |
| Polyethylene Glycol | 1.0 max % m/m |
| EO/Alcohol ratio | 2.7-3.0 mol/mol |
| Hydroxyl number | 166-172 mg KOH/g |
| Molecular mass | 326-338 g/mol |

(12) NEODOL 25-5—Typical Properties (Average 5 Moles EO)

| Property | Value |
| --- | --- |
| Polyethylene Glycol | 2 max % m/m |
| EO/Alcohol ratio | 4.6-5.4 mol/mol |
| Hydroxyl number | 127-137 mg KOH/g |
| Molecular mass | 409-442 g/mol |

(13) NEODOL 25-7—Typical Properties (Average 7 Moles EO)

| Property | Value |
| --- | --- |
| Polyethylene Glycol | 2 max % m/m |
| EO/Alcohol ratio | 6.5-7.6 mol/mol |
| Hydroxyl number | 104-114 mg KOH/g |
| Molecular mass | 492-540 g/mol |

(14) NEODOL 25-9—Typical Properties (Average 9 Moles EO)

| Property | Value |
| --- | --- |
| Polyethylene Glycol | 2 max % m/m |
| EO/Alcohol ratio | 8.3-9.8 mol/mol |
| Hydroxyl number | 88-98 mg KOH/g |
| Molecular mass | 573-638 g/mol |

(15) NEODOL 45-4—Typical Properties (Average 4 Moles EO)

| Property | Value |
| --- | --- |
| Polyethylene Glycol | 1.0 max % m/m |
| EO/Alcohol ratio | 3.7-4.3 mol/mol |
| Hydroxyl number | 136-146 mg KOH/g |
| Molecular mass | 384-412 g/mol |

(16) NEODOL 45-6.8—Typical Properties (Average 6.8 Moles EO)

| Property | Value |
| --- | --- |
| Polyethylene Glycol | 2 max % m/m |
| EO/Alcohol ratio | 6.3-7.4 mol/mol |
| Hydroxyl number | 103-113 mg KOH/g |
| Molecular mass | 498-547 g/mol |

(17) NEODOL 45-7—Typical Properties (Average 7 Moles EO)

| Property | Value |
| --- | --- |
| Polyethylene Glycol | 2 max % m/m |
| EO/Alcohol ratio | 6.8-8.0 mol/mol |
| Hydroxyl number | 98-108 mg KOH/g |
| Molecular mass | 519-573 g/mol |

(18) NEODOL 1-9—Typical Properties (Average 9 Moles EO)

| Property | Value |
| --- | --- |
| Polyethylene Glycol | 2 max % m/m |
| EO/Alcohol ratio | 8.4-9.7 mol/mol |
| Hydroxyl number | 94-104 mg KOH/g |
| Molecular mass | 539-597 g/mol |

As evident from the examples of blends suitable for use as the non-ethoxylated linear C9-C17 primary alcohol blend and ethoxylated blends thereof, small amounts of other linear primary alcohols may be present, including for example, side products resulting from the manner of providing the blend. The non-ethoxylated and ethoxylated linear primary alcohol blends useful in the composition of the invention include alcohols having C9-C17 chain lengths as a major component which together provides a majority of the alcohols present. No non-linear alcohols are present in the blend.

Nonlimiting examples of hydrophilic polymers useful herein include those based on acrylic acid and acrylates, such as, for example, described in U.S. Pat. Nos. 6,593,288, 6,767,410, 6,703,358 and 6,569,261. Suitable polymers are sold under the trade name of MIRAPOL SURF S by Rhodia. A preferred polymer is MIRAPOL SURF S-500.

A superwetter is optionally included in the composition to enhance the maintenance of the wet film provided. A superwetter may thereby assist in decreasing the time of spreading. Examples of superwetters suitable for inclusion in the composition hydroxylated dimethylsiloxanes such as Dow Corning Q2-5211 (Dow Corning, Midland, Mich.). The superwetter(s) may be present (in addition to any other surfactant in the composition) in an amount of 0 to about 5 wt. %; preferably from about 0.01 to about 2 wt. %, and most preferably from about 0.1 wt. % to about 1 wt. %.

Fragrances and aromatic substances can be included in the composition to enhance the surrounding atmosphere.

In one embodiment, a gel composition comprises less than 6 wt. % fragrance. In another embodiment, the gel composition comprises from 0 wt. % to 6 wt. % fragrance. In another embodiment still, the gel composition comprises from 0 wt. % to about 5 wt. % fragrance. In yet another embodiment, the gel composition comprises from about 2 wt. % to about 5 wt. % fragrance.

In one embodiment, a solid composition comprises less than 10 wt. % fragrance. In another embodiment, the solid composition comprises from 0 wt. % to 10 wt. % fragrance. In another embodiment still, the solid composition comprises from 2 wt. % to about 8 wt. % fragrance. In yet another embodiment, the gel composition comprises from about 4 wt. % to about 7 wt. % fragrance.

The composition according to the invention sticks to hard surfaces through self-adhesion. The solid, gel and gel-like materials are dimensionally stable so that they do not "run" or "drip" through a plurality of streams of water flowing thereover. It is thought that consumers prefer such a composition because the adhesion and shape of the composition remain intact even through a plurality of water rinses. Exemplary compositions comprising mineral oil are described in Table B, below:

TABLE B

Exemplary Compositions Comprising Mineral Oil

| INGREDIENTS | SAMPLE 1 | SAMPLE 2 | SAMPLE 3 | SAMPLE 4 |
|---|---|---|---|---|
| $C_{22}$ Ethoxylated Alcohol (30 EO) | 13 | 13 | 13 | 13 |
| $C_{16-18}$ Ethoxylated Alcohol (30 EO) | 13 | 13 | 13 | 13 |
| Preservative | 0.15 | 0.15 | 0.15 | 0.15 |
| Dionized Water | 44.85 | 44.75 | 44.35 | 43.85 |
| Mineral Oil | 0 | 0.1 | 0.5 | 1.0 |
| Glycerine | 5 | 5 | 5 | 5 |
| Polyethylene Glycol 6000 | 1 | 1 | 1 | 1 |
| Sodium lauryl ether sulfate | 18 | 18 | 18 | 18 |
| Fragrance | 5 | 5 | 5 | 5 |
| Total Wt. % | 100 Wt. % | 100 Wt. % | 100 Wt. % | 100 Wt. % |

Transport of Active Ingredients

As described supra, the composition of the invention may be applied directly on the surface of a sanitary object to be cleaned, such as a toilet bowl, shower or bath enclosure, or the like, and self-adheres thereto through a plurality of streams of water flowing over the self-adhering composition, e.g. flushes or showers. Each time water flows over the composition, a portion of the composition is released onto the surface to which the composition adheres as well as into the water to provide long term cleaning, disinfecting, fragrancing, stain prevention, surface modification, UV protection, whitening, bleaching, and the like. It is thought that any residual benefits may be obtained from the composition through the inclusion of ingredients described above which provide for the spreading and/or transport of the composition along the hard surface to areas wherein the composition was not originally deposited. More specifically, the composition, and thus the active agents of the composition, spread out from or are delivered from the initial composition placement in direct contact with the surface to coat an extended adjoining area on the surface. Motions of the surface of a liquid are coupled with those of the subsurface fluid or fluids, so that movements of the liquid normally produce stresses in the surface and vice versa. The movement of the surface and of the entrained fluid(s) caused by surface tension gradients is called the Marangoni effect (IUPAC Compendium of Chemical Terminology, 2nd Edition, 1994). Thus, the composition of the invention provides that liquid flows along a liquid-air interface from areas having low surface tension to areas having higher surface tension. The Marangoni flow is macroconvection, i.e., the gradient in the interfacial tension is imposed on the system by an asymmetry, as opposed to microconvection where the flow is caused by a disturbance that is amplified in time (an instability). Thus, upon a flow of water over the composition of the invention, the composition spreads outward to cover extended adjoining surface areas as opposed to only the local area covered by or immediately adjacent the composition.

More specifically, it is thought that this effect is observed due to mass transfer on, or in, a liquid layer due to differences in surface tension on that liquid layer. Without wishing to be limited by theory, it is thought that because a liquid with a relatively high surface tension pulls more strongly on the surrounding liquid compared to a liquid with a relatively low surface tension, a surface tension gradient will cause liquid to flow away from regions of relatively low surface tension towards regions of relatively high surface tension. Such property, the Marangoni effect, is used in high-tech semiconductor wafer processing. Nonlimiting examples include U.S. Pat. Nos. 7,343,922; 7,383,843; and 7,417,016.

Those of skill in the art will appreciate that a dimensionless unit often referred to as the Marangoni number may be used to estimate the Marangoni effect, and other transport properties, of a material. One of the factors which may be used to estimate the Marangoni effect of a material, the Marangoni number, may be described by Eq. 1. One of skill in the art will appreciate that the Marangoni number provides a dimensionless parameter which represents a measure of the forces due to surface tension gradients relative to viscous forces.

$$M_a = -\Gamma(d\sigma/dc)/D\mu \qquad \text{Marangoni number,}$$

Where $M_a$ is the Marangoni number
$\Gamma$ is the surface excess concentration of surfactant (mol/m$^2$)
$\sigma$ is the surface tension (N/m)
c is the bulk surfactant concentration (mol/m$^3$)
$\mu$ is the bulk dynamic viscosity (Pascal seconds)
D is the bulk surfactant diffusion coefficient (m$^2$/s)

As described supra, there exist a number of compositions that are used to transport active ingredients around a surface. However, most of the aforementioned compositions rely on gravity or the adhesion-cohesion of liquids as the lone mechanisms for transporting the composition around the surface. Similarly, traditional liquid bathroom cleaners or similar compositions in the bath cleaning arts, for example, often require the user to use a brush, other implement, to manually spread the composition around the surface.

Surprisingly, it was discovered that, despite the complexity associated with transport phenomena, the transport properties of a composition could be enhanced through the addition of specific surfactants and other ingredients, to the composition. Even more surprisingly, the composition may be used as a vehicle for active ingredients when the composition is in the presence of a liquid layer.

With respect to a hard surface, such as a toilet bowl, it is thought that by providing a composition according to the present invention, one may be able to provide consumers with additional benefits of limiting the amount of touching or other interaction between the consumer and the toilet bowl. Such minimal interaction may be achieved by taking advantage of the composition's ability to move from one area of the toilet (or other hard surface) via gradients in surface tension which may be induced by the surfactants. Thus, it is thought that when a user flushes a toilet, the interaction of the liquid layer (from the flush) with the composition will cause the gel composition to migrate along the surface tension gradient, thus moving the composition around the toilet.

One of skill in the art will appreciate that the transport mechanism described above may be used with any hard surface that is provided with a liquid layer and is not necessarily limited to use in a toilet bowl. For example, it is hypothesized that a user may be able to provide a composition to the surface of a sink, window, drain, or any other hard surface on which water, or other liquid, may be provided. Additional exemplary surfaces are described throughout.

Considerations for Treatment of Hard Surfaces

The self-spreading of the composition to provide a coating effect and residual benefits from active treating agents, is based on the surfactant(s) present in the composition. Nonlimiting factors which may be thought to affect the speed and distance of the self-spreading, in addition to the essential requirements of direct contact of the composition with the surface to be treated and a flow of water over and around the composition, are the amount and type of surfactant present, in addition to and the amount or rate of dissolution of the surfactant in the water flow.

It is surprisingly discovered that when the surfactant amount and dissolution are controlled as described above, the product is capable of covering an extended area outward 360° from the area of initial product application. Further, in embodiments including active ingredients, also described above, the composition may provide an initial and/or further residual treatment of a surface. The speed of spreading is significant since the extent of spreading as desired must be complete prior to drying of the water on the surface since the water is a necessary component in providing the continuous film.

Method of Use

As described above, the present invention compositions may be used to provide immediate and/or residual benefits to a hard surface upon application to that surface wherein the surface will be subject to water or some other liquid which will provide a layer for a surface energy gradient.

In one embodiment the present invention composition may be comprised of the following steps: (1) Application of one or more doses of the composition onto a hard surface; (2) Exposure of the hard surface, and subsequently the one or more doses of composition, to a liquid layer to provide a spread out and dissipated composition layer. The method for using the product may further comprise the optional steps: (3) Exposure of the hard surface, and subsequently the spread out and dissipated composition layer to a liquid layer to provide a further spread out and dissipated composition layer. One of skill in the art will appreciate that (3) may be repeated indefinitely until the composition is completely dissipated. In some embodiments, the liquid layer is water.

As described supra, the hard surface may be selected from the group consisting of: ceramic, glass, metal, polymer, fiberglass, acrylic, stone, the like and combinations thereof.

A liquid layer may be provided through any means that is suitable for the intended function. For example, in a toilet bowl, a dose of composition may be applied to the inside surface of the toilet bowl (a ceramic hard surface) and the toilet may be flushed to provide the liquid layer that is necessary to facilitate the transport of the composition around the toilet bowl. In another example, a dose of composition may be applied to the outside surface of a window. The outside surface of the window may be sprayed with water by the user using a hose or power washer, or rain may deposit a layer of water to the window. In yet another example, a dose of composition may be applied to the inside of a sink or drain pipe. The user may simply activate the faucet to provide a layer of water to the sink or drain pipe. In still another example, a dose of composition may be applied to the wall of a shower. The user may activate the shower to provide a liquid layer to the surface. In yet another example, it is envisioned that the liquid layer may also be provided with steam or a relatively high humidity.

One of skill in the art will appreciate that the different applications and embodiments of the present invention composition may be provided with different active ingredients or benefit agents which may vary depending on the desired application.

Method of Use: Dispensing Considerations

There exist applicators for gel-like substances. For example, PCT Int. Pat. App. WO 03/043906 and WO 2004/043825 disclose exemplary dispensing devices. However, while the aforementioned dispensers succeed in applying an adhesive gel-like substance to a surface, some users may find that the inability to provide consistent dosing frustrating. Specifically, consumers realize that overapplication of the product may be wasteful and lead to the purchase of unnecessary refills, while underapplication of the product may minimize the efficacy of the composition.

A nonlimiting exemplary dispenser that is capable of providing metered doses of a composition that may be compatible with the present invention compositions is described in U.S. Pat. App. No. 2007/0007302A1. Without wishing to be limited by theory, it is thought that consumers may prefer to provide the compositions of the present invention in unitized, discrete doses because such a device is relatively easy to use compared to devices wherein the consumer controls the dose size.

Further, one of skill in the art will appreciate that, when used in conjunction with a metered dispenser, the dispenser may provide doses of the composition in any volume and/or size and/or dose that is suitable for the intended application. Similarly, the shape of the dispenser may be any shape that is desired. For example, FIG. 1 illustrates an exemplary embodiment of a dispenser 10 that may be used to dispense gel composition 20 according to the present invention. The dispenser 10 comprises a cylindrical body 11 and a gel composition 20 contained therein. The dispenser 10 further comprises a resistive push-button 13 which fits a user may push into a guide hole 14, and then slide a guide member 15 in the negative-y direction to push gel composition 20 towards the dispenser mouth 12. Upon moving the guide member 15 a predetermined distance, the push-button 13 may then "pop" out of the next guide hole 14 to allow for a precise dose of composition 20 to be dispensed. The cross-section 17-17 of the dispenser 10 may be any shape that is desirable for the intended purpose. In one embodiment, the cross section 17-17 may be annular.

Nonlimiting examples of cross-sectional shapes may be selected from: squares, circles, triangles, ovals, stars, the like, and combinations thereof.

In one embodiment, a composition according to the present invention may be provided in a dispenser wherein the dispenser provides unitized doses. In a particular embodiment, the unitized dose is from about 4 g/dose to about 10 g/dose. In another embodiment, the unitized dose is from about 5 g/dose to about 9 g/dose. In yet another embodiment, the dispenser may provide from about 6 to about 8 g/dose unitized doses. In still another embodiment, the dispenser may provide from about 3 to about 12 unitized doses. In some embodiments, the dispenser may be refilled with additional composition.

In embodiments wherein the composition is a solid, or a malleable solid, an exemplary method and apparatus for dispensing is described in U.S. Pat. App. No. 2008/0190457.

Experimental Results and Data

Samples

Samples 1-13 comprise a base ingredient set in addition to a surfactant. It should be noted that the amount of deionized water in the base ingredient set is adjusted to accommodate the additional surfactant in Samples 1-13. The Scrubbing Bubbles Sample describes an embodiment of a current product (Scrubbing Bubbles Toilet Gel "Citrus Scent", S.C. Johnson & Son, Racine, Wis.). The U.S. Pat. No. 6,667,286 samples are derived from Example 1 of U.S. Pat. No. 6,667,286. '286 (1) includes the Rhodopol component. '286 (2) is a sample that is made with ingredients at the midpoint of the described ranges. Measurements are made to the samples for different properties. Surprisingly, the samples comprising the surfactant, and other ingredients according to the present invention samples provide an ideal combination of various properties which are described in greater detail below:

Base Ingredient Set ("Base"):

| Ingredient | Wt. % |
| --- | --- |
| Deionized Water | 64.000000 |
| $C_{22}$ Ethoxylated Alcohol (30 EO) | 13.000000 |
| $C_{16-18}$ Ethoxylated Alcohol (30 EO) | 13.000000 |
| Glycerine, USP, 99.5% | 5.000000 |
| Quest ® F560805 | 5.000000 |

Samples

| Sample | Surfactant | Wt. % |
| --- | --- | --- |
| 1 | Alkyl Polyglycoside 425 N | 2.00 |
| 2 | Pluronic ® F127 | 1.00 |
| 3 | Tergitol ® 15-S-12 | 1.03 |
| 4 | Sodium Lauryl Ether Sulfate 2EO, 70% | 1.43 |
| 5 | Q2-5211 | 1.67 |
| 6 | Leutensol ® XL140 | 1.00 |
| 7 | Leutensol ® XP 30 | 1.00 |
| 8 | Aerosol ® OT-NV | 1.20 |
| 9 | Macat ® AO-12 | 3.33 |
| 10 | Macat ® AO-8 | 3.51 |
| 11 | Tegopren ® 6922 | 2.00 |
| 12 | Alkyl Polyglycoside 425 N | 4.00 |
| 13 | Sodium Lauryl Ether Sulfate 2EO, 70% | 8.00 |
| '286 (1) | Example 1 of 6,667,286 - Rhodopol | 6.00 |
| '286 (2) | Example 1 of 6,667,286 - Midpoints of ranges | 6.00 |
| Scrubbing Bubbles | Quest ® F560805 | 12.60 |

Surface Spreading

As described supra, the present invention compositions provides the unexpected benefit over existing compositions of, inter alia, increased mobility and transport. Exemplary compositions are made according to the Detailed Description and are tested for surface spreading using the "Surface Spreading Method" described below.

Surprisingly, it is noticed that the addition of the surfactants provide a significant increase in transport of the compositions. In one embodiment, the compositions of the present invention provide a transport rate factor of less than 55 seconds. In another embodiment, the compositions of the present invention provide a transport rate factor of less than about 50 seconds. In still another embodiment, the compositions of the present invention provide a transport rate factor of from about 0 seconds to about 55 seconds. In another embodiment, the compositions of the present invention provide a transport rate factor of from about 30 seconds to about 55 seconds. In yet still another embodiment, the compositions of the present invention provide a transport rate factor of from about 30 seconds to about 50 seconds. In still another embodiment, the compositions of the present invention provide a transport rate factor of from about 30 seconds to about 40 seconds.

Results for the surface spreading (Transport Rate Factor) of a product is reported in Table C below.

The surface spreading of a product is measured by the Surface Spreading Test described below.

TABLE C

Surface Spreading Measurements

| Sample | Transport Rate Factor |
| --- | --- |
| 1 | 33.2 |
| 2 | 47.7 |
| 3 | 53.3 |
| 4 | 50.5 |
| 5 | 30.4 |
| 6 | 50.1 |
| 7 | 46.3 |
| 8 | 36.9 |
| 9 | 37.0 |
| 10 | 42.7 |
| 11 | 56.9 |
| 12 | 38.5 |
| 13 | 40.2 |
| Base | 50.1 |
| '286 (1) | 65.9 |
| Scrubbing Bubbles | 39.1 |

Composition Adhesion

In addition to the mobility of the composition, it is surprisingly discovered that the ability of the composition to adhere to a hard surface provides additional unexpected benefits, such as product longevity during use. A product must have an ability to adhere to a surface for a period of at least 5 hours, as measured by the adhesion test described below. In one embodiment, a product has a minimum adhesion of greater than about 8 hours. In another embodiment, a product has a minimum adhesion of from about 8 hours to about 70 hours.

Results for the minimum adhesion of a product is reported in Table D below.

The minimum adhesion of a product is measured by the Adhesion Test described below.

TABLE D

Minimum Adhesion Measurements

| Sample | Adhesion Time (Hours) |
| --- | --- |
| 1 | >64 |
| 2 | >64 |
| 3 | >64 |
| 4 | >64 |
| 5 | >64 |
| 6 | >88 |
| 7 | >64 |
| 8 | >64 |
| 9 | >64 |
| 10 | >64 |
| 11 | >88 |
| 12 | >64 |
| 13 | >88 |
| Base | >64 |
| '286 (1) | 6.0 |
| '286 (2) | 7.5 |
| Scrubbing Bubbles | 21.0 |

Composition Gel Temperature

It is thought that an additional property which is important to compositions is the ability to maintain its form despite being subject to relatively high temperatures. Similarly to adhesion, the ability to maintain its form, and being resistant to melting. Specifically, this metric measures the temperature at which the composition transitions to a viscosity of greater than 100 cps as the composition cools. Further, having a relatively high composition gel temperature may provide processing, manufacturing, transport, and packaging advantages to producers.

In one embodiment the composition has a gel temperature of greater than 50° C. In another embodiment, the composition has a gel temperature of from about 50° C. to about 80° C. In another embodiment still, the composition has a gel temperature of from about 50° C. to about 70° C.

The composition gel temperature is measured by the Gel Temperature Test described below.

Results for the composition gel temperature of a product is reported in Table E below.

The minimum adhesion of a product is measured by the Gel Temperature Test described below.

TABLE E

Gel Temperature Measurements

| Sample | Gel Temperature (° C.) |
|---|---|
| 1 | 72.3 |
| 2 | 67.9 |
| 3 | 72.9 |
| 4 | 72.2 |
| 5 | 70.0 |
| 6 | 71.0 |
| 7 | 71.8 |
| 8 | 65.6 |
| 9 | 68.0 |
| 10 | 71.4 |
| 11 | 68.4 |
| 12 | 74.3 |
| 13 | 62.1 |
| Base | 70.5 |
| '286 (1) | 68.9 |
| '286 (2) | 72.7 |
| Scrubbing Bubbles | 70.5 |

Composition Viscosity

In some nonlimiting embodiments, the composition of the invention is in the form of a self-adhering gel or gel-like composition for treating hard surfaces. In the embodiments wherein the compositions are self-adhering gels, the viscosity of the composition is from about 15,000 cps to about 100,000 cps. In another embodiment, the viscosity is from about 25,000 cps to about 80,000 cps. In yet another embodiment, the viscosity is from about 30,000 cps to about 60,000 cps.

The composition gel temperature is measured by the Viscosity Test described below. The viscosity is measured based on 80 Pascals (Pa·s) at 25° C. at 10 shear.

TABLE F

Viscosity Measurements

| Sample | Viscosity (Pa · s) |
|---|---|
| 1 | 213 |
| 2 | 187 |
| 3 | 233 |
| 4 | 155 |
| 5 | 270 |
| 6 | 187 |
| 7 | 282 |
| 8 | 199 |
| 9 | 239 |
| 10 | 208 |
| 11 | 104 |
| 12 | 168 |
| 13 | 349 |
| Base | 143 |
| '286 (1) | 309 |
| '286 (2) | 436 |
| Scrubbing Bubbles | 351 |

Test Methods

Surface Spreading Method

The "transport rate factor" is measured as described below.

A 12"×12" pane of frosted or etched glass is mounted in a flat-bottomed basin that is large enough to support the pane of glass. The basin is provided with a means for drainage such that water does not accumulate on the surface of the pane of glass as the experiment is performed at a room temperature of approximately 22° C. in ambient conditions. The pane of glass is supported on top of the bottom of the basin of water using 4"×4" ceramic tiles—one tile at each side of the bottom edge of the pane. The middle 4 inches of the pane is not touching the bottom, so that water can run down and off the glass pane. The pane of glass is juxtaposed such that pane of glass is at an angle of approximately 39° from the bottom of the basin.

The glass pane is provided with 0.5 inch measurement markers from a first edge to the opposing edge.

A glass funnel (40 mm long×15 mm ID exit, to contain >100 ml) is provided approximately 3.5" over the 9" mark of the pane of glass.

The pane of glass is cleaned with room temperature water to remove trace surface active agents. The cleaned pane of glass is rinsed until there is no observable wave spreading on the pane.

A sample of approximately 7 g. (approximately 1.5" diameter circle for gels) of composition is applied to the pane of glass at the 0 mark. Four beakers (approximately 200 mL each) of water (are slowly poured over the top of the glass pane at the 9" height point and is allowed to run down the pane of glass to condition the composition.

After about one minute, the funnel is then plugged and is provided with approximately 100 mL of water. An additional 100 mL of water is slowly poured onto the glass pane at approximately the 9" marker. After approximately 10 seconds, the stopper is removed and a timer is started as the water in the funnel drains onto the pane of glass.

A wave on the surface of the draining water film above the composition is observed to creep up the glass and the time for the composition to reach the 5" marker is recorded.

The test is repeated for 10 replicates and the time in seconds is averaged and reported as the "transport rate factor" (time in seconds).

Adhesion Test

The ability of a composition to adhere to an exemplary hard surface is measured as described below.

A workspace is provided at a temperature of from about 86° F. to about 90° F. The relative humidity of the workspace is set to from about 40% to about 60%.

A board comprising twelve 4.25"×4.25" standard grade while glossy ceramic tiles arranged in a 3 (in the y-direction)×4 (in the x-direction) configuration (bonded and grouted) to a plexi-glass back is provided.

The board is rinsed with warm (about 75° F. to about 85° F.) tap water using a cellulose sponge. The board is then re-rinsed thoroughly with warm tap water. A non-linting cloth (ex. Kimwipe®, Kimberly Clark Worldwide, Inc., Neenah, Wis.) saturated with isopropanol is used to wipe down the entire tile board.

The board is juxtaposed to be in a horizontal position (i.e., such that the plane of the board is flat on the floor or lab bench).

Samples approximately 1.5" in diameter and weighing from about 5.5 g to about 8.0 g are provided to the surface of the board such that the bottom of the sample touches the top-most, horizontally oriented (i.e., in the x-direction), grout line of the board. Samples are spaced approximately 2" apart from each other. A permanent marker is used to draw a straight line (parallel to the x-direction) approximately 0.75" below the top-most grout line.

The board is juxtaposed to then be in the vertical position (i.e., such that the plane of the board is perpendicular with the floor or lab bench). A timer is started as the board is moved to the vertical position. The time that a sample takes for the sample to slide down the tile a distance of about 1.5 times the diameter of the sample is measured, recorded as the "sample adhesion time."

Viscosity Test

A Brookfield temperature controlled Cone/Plate Viscometer (Brookfield Engineering Laboratories, Inc., Middleboro, Mass.) is used according to the manufacturer's specifications. The specific parameters used on the device are: Shear rate of 10; C-25-1 Cone; and an 80° C. to 25° C. temperature ramp-down for 240 seconds. The device provides the viscosity measurement in Pascals (Pa·s).

Gel Temperature Test

A Brookfield temperature controlled Cone/Plate Viscometer (Brookfield Engineering Laboratories, Inc., Middleboro, Mass.) is used according to the manufacturer's specifications. The specific parameters used on the device are: Shear rate of 10; C-25-1 Cone; and an 80° C. to 25° C. temperature ramp-down for 240 seconds. The gel temperature is reported as the temperature at which the composition transitions to a viscosity of greater than 100 cps as the composition cools.

Example 1: Transport Along Water Film

To illustrate the surprising range and speed of the Marangoni effect provided by the composition of the invention, an experiment is described below.

A conventional white toilet bowl (Kohler Co., Kohler, Wis.) is cleaned twice using a conventional cleaner ("The Works" Toilet and Bathroom Cleaner (20% HCl)) and brush to insure that no material is present on the ceramic surface of the toilet bowl. A 5% solution of blue dye in water is sprayed onto the surface of the toilet bowl to provide an essentially even blue coating over the entire bowl surface above the water line. The dye remains a substantially uniform blue and is substantially stationary and non-moving upon visual observation for about one minute. The toilet is flushed and the dye rinsed away.

A sample of composition weighing approximately 7 g. as set out above as "Sample 2" is applied as a single dollop to one location in an upper side of the toilet bowl above the water line. The toilet is flushed so water runs down over the composition and along the inside surface of the toilet. Thereafter, the blue dye solution was again sprayed over the toilet bowl surface to cover the entire area above the water line as indicated by the blue color. Upon visual observation for about two minutes, it is observed that the blue dye moved away from the applied composition in all directions by material emanating from the composition as evident by the now visual white surface of the bowl. By the end of two minutes, the composition covered approximately one half of the bowl surface as evident from the essential absence of blue dye from the surface. Without wishing to be limited by theory, it is thought that the spread of the composition occurred through the Marangoni effect.

Due to the spread of the composition over the bowl, the desired action sought by the active agent(s) (e.g. cleaning, disinfecting and/or fragrancing) present in the composition is achieved over an extended area and provides residual benefit on the surface to prevent build up from subsequent use and prevent water stains.

Example 2: Effect of Mineral Oil on Adhesion of Gel Compositions

Samples of compositions (approximately 7 g.) according to the present invention containing 0, 0.1, 0.5 and 1 wt. % (Samples E-H, respectively) are tested according to the Adhesion Test Method described herein. Two trials of each of Samples E-H is applied to a tile board according to the adhesion test method described below. FIGS. 2A-E are photographs of the tile board at times of 8.5 hours, 9.5 hours, 11 hours, 12.5 hours, and 15 hours, respectively. Surprisingly, it is discovered that the compositions with a relatively lower wt. % mineral oil tend to have lower adhesion times than samples with a relatively higher wt. % mineral oil.

Tests Re Non-Ethoxylated and Ethoxylated Linear Primary Alcohol Blends

It is desirable to keep the gel point of the composition balanced between minimizing processing temperatures during manufacture of the product while maintaining gel structure to insure increased adhesion to improve product performance. This property is to be maintained under shipping, storage and use conditions. The use of the linear C9-C17 primary alcohol blends, and ethoxylated blends thereof, serve to reduce the gel point to a desired value while having a minimal effect on the properties of adhesion, force to actuate and maximum gel viscosity.

Figure 3:
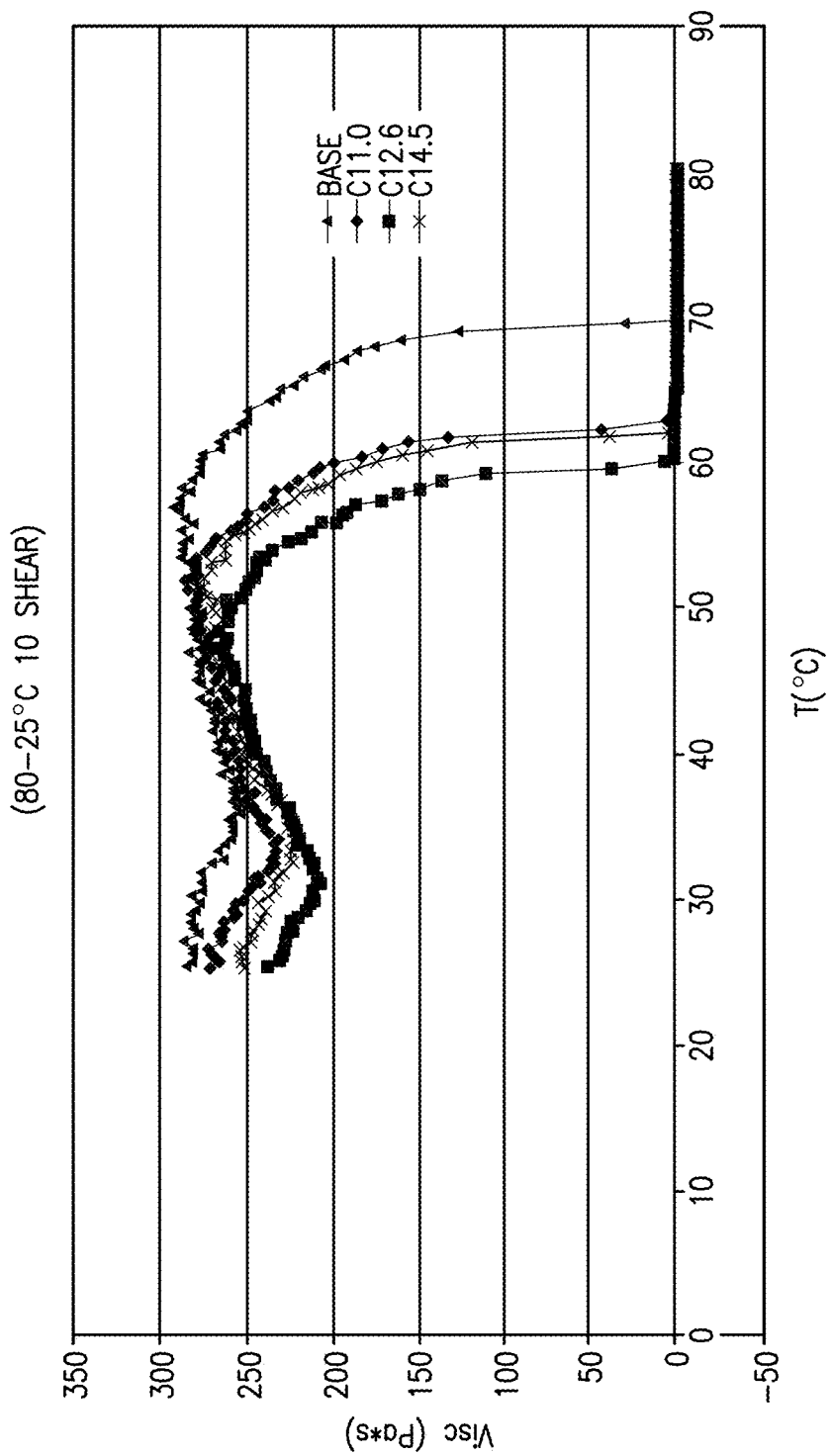
FIG. 3 is a graph showing the downward shift in gel point as a function of a blend of linear primary alcohols as to four examples, i.e., three blends of linear primary alcohols having, respectively, an average chain length of 11.0, 12.6 and 14.5 carbons, and a base formula which contains no alcohol.

FIG. 3 is a graph as to four tested composition formulas (which are identical as to components except as to the alcohol blend included therein) showing the downward shift in gel point as a function of chain length of various primary alcohol blends, i.e., alcohols having an average chain length of 11.0 carbons (C11.0), 12.6 carbons (C12.6) and 14.5 carbons (C14.5). For comparison, a base formula (Base) which contains no alcohol is also shown.

Figure 4:
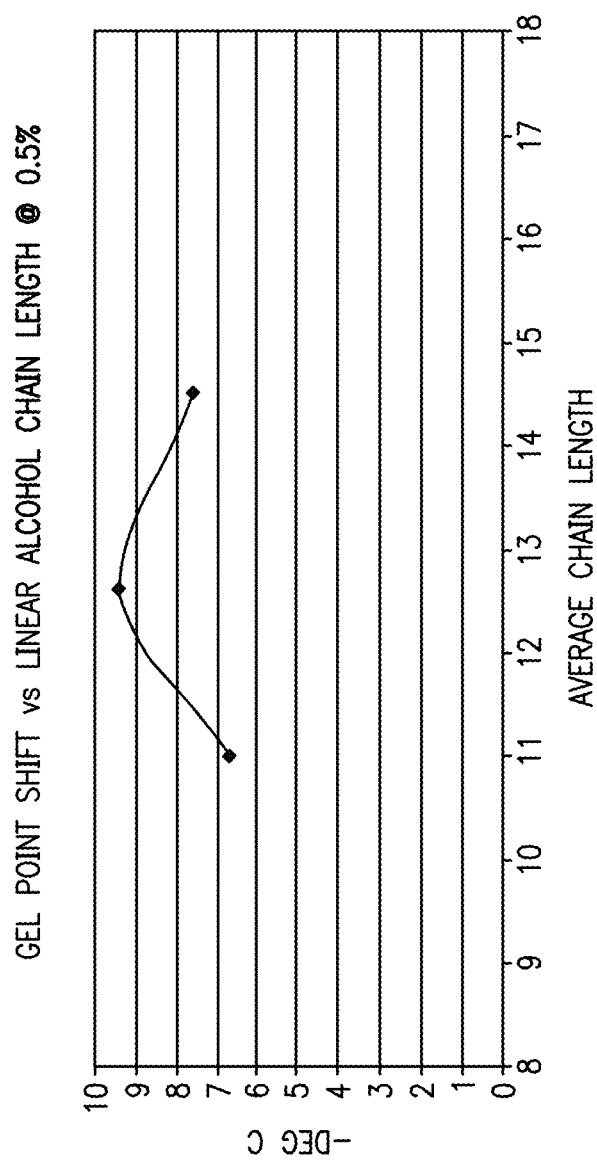
FIG. 4 is a graph showing the optimum gel point suppression in the region of C13 (carbon length of 13) based on the downward shift in gel point as a function of chain length based on the results shown in FIG. 3.

From the downward shift in gel point as a function of chain length of the alcohols of FIG. 3, an optimum gel point suppression is obtained in the region of C13 as shown in FIG. 4. As shown in FIG. 4, for chain length C11 the gel point shift was 6.7, for chain length C12.6 the gel point shift was 9.4, and for chain length C14.5 the gel point shift was 7.6.

Figure 5:
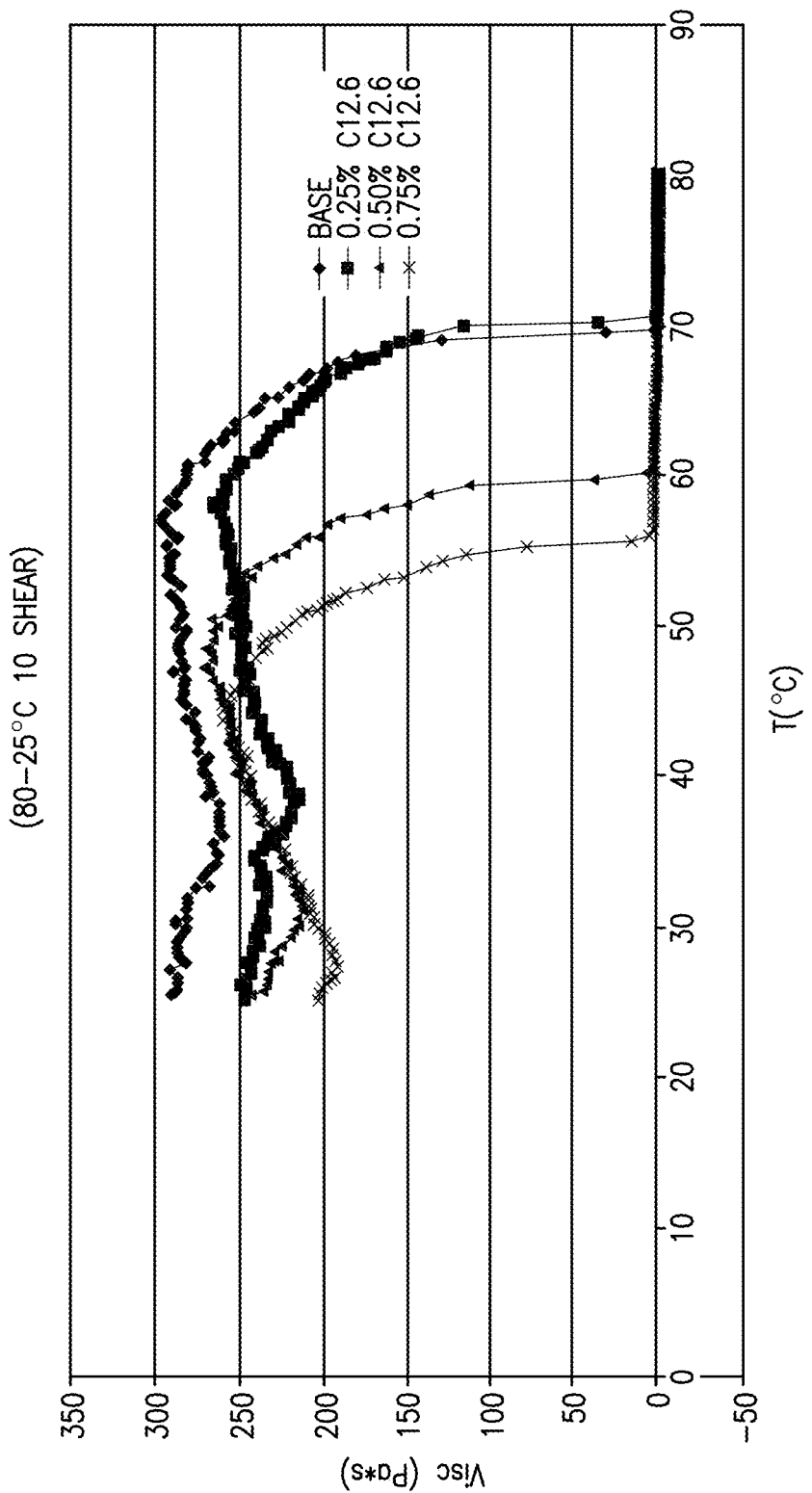
FIG. 5 is a graph showing the downward shift in gel point as a function of the amount of a blend of linear primary alcohols having an average chain length of 12.6 carbons.

The graph shown in FIG. 5 shows the downward shift in gel point as a function of the amount of C12.6 primary alcohol blend present. As shown in the key to FIG. 5, the amounts were 0.25% by wt., 0.50% by wt. and 0.75% by wt. of a C12.6 alcohol blend in three respective formulas which were otherwise identical. For comparison, a base formula containing no alcohol is also shown.

Figure 6:
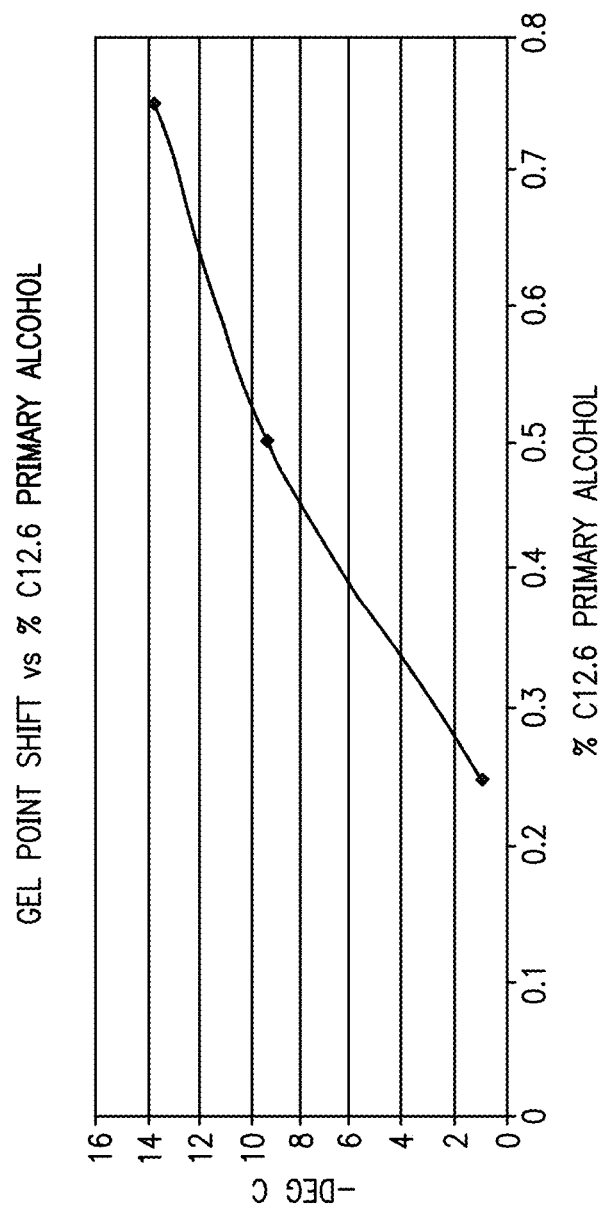
FIG. 6 is a graph showing the gel point suppression of the blend of linear primary alcohols having an average chain length of 12.6 carbons based on the downward shift in gel point as a function of the percent of C12.6 primary alcohols present.

In FIG. 6, the downward shift in gel point as a function of the percent of C12.6 present illustrates the ability to obtain good control of gel point suppression. For the formulas including NEODOL 23 (C12.6 average) in the amount of 0.25%, the gel point shift was 0.9; in the amount of 0.50%, the gel point shift was 9.4; and for the amount of 0.75%, the gel point shift was 13.7. In formulas where gel point suppression is not sought by inclusion of the linear primary alcohol blends, a sharp transition from liquid to cubic phase of the gel is present. Suppression of gel points with a primary alcohol blend can result in a phase transition stage which interferes with the cubic phase of the gel. This gives a temperature range where there is thickening of the product before a sharp viscosity increase is obtained. This transition phase is not desirable. In considering in FIG. 5 the viscosity data at amounts of 0.25%, 0.50% and 0.75% and the range of 0 to 10 Pa's, this phase transition area can be seen.

Figure 7:
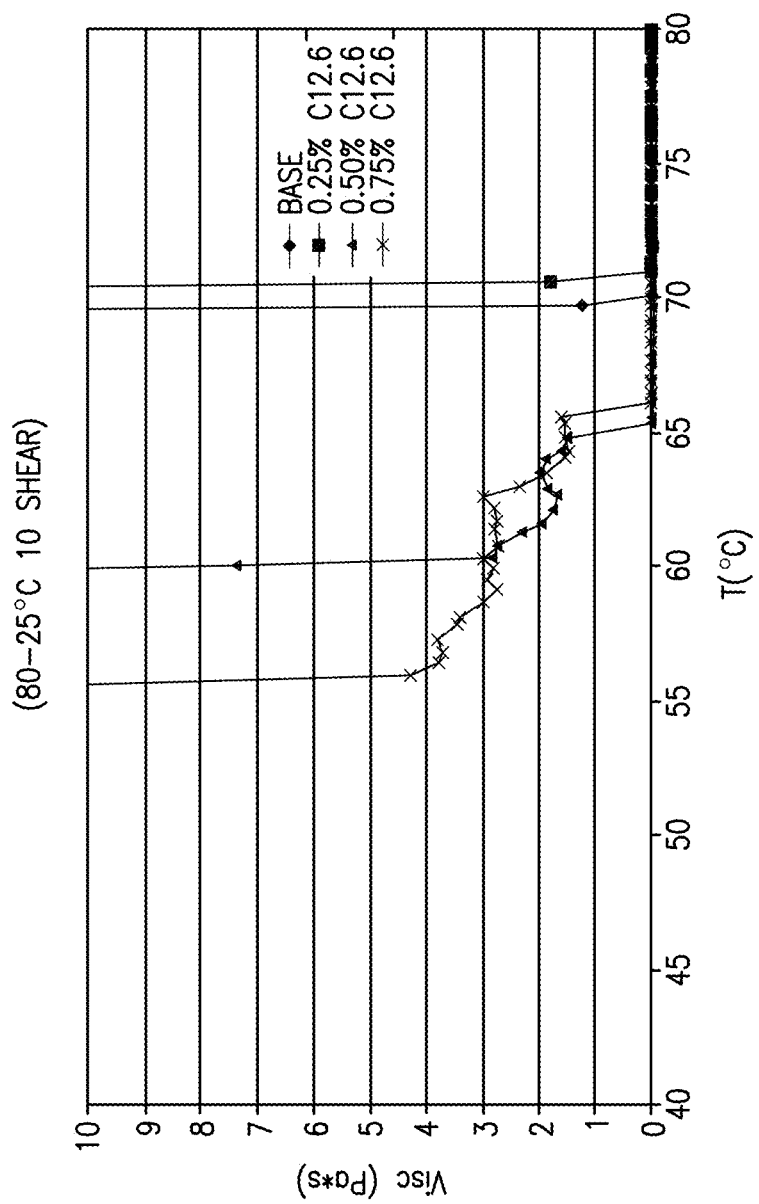
FIG. 7 is a graph showing that as the amount of linear primary alcohol is increased, the phase transition region between a liquid phase to a cubic phase becomes an increasing consideration.
Figure 8:
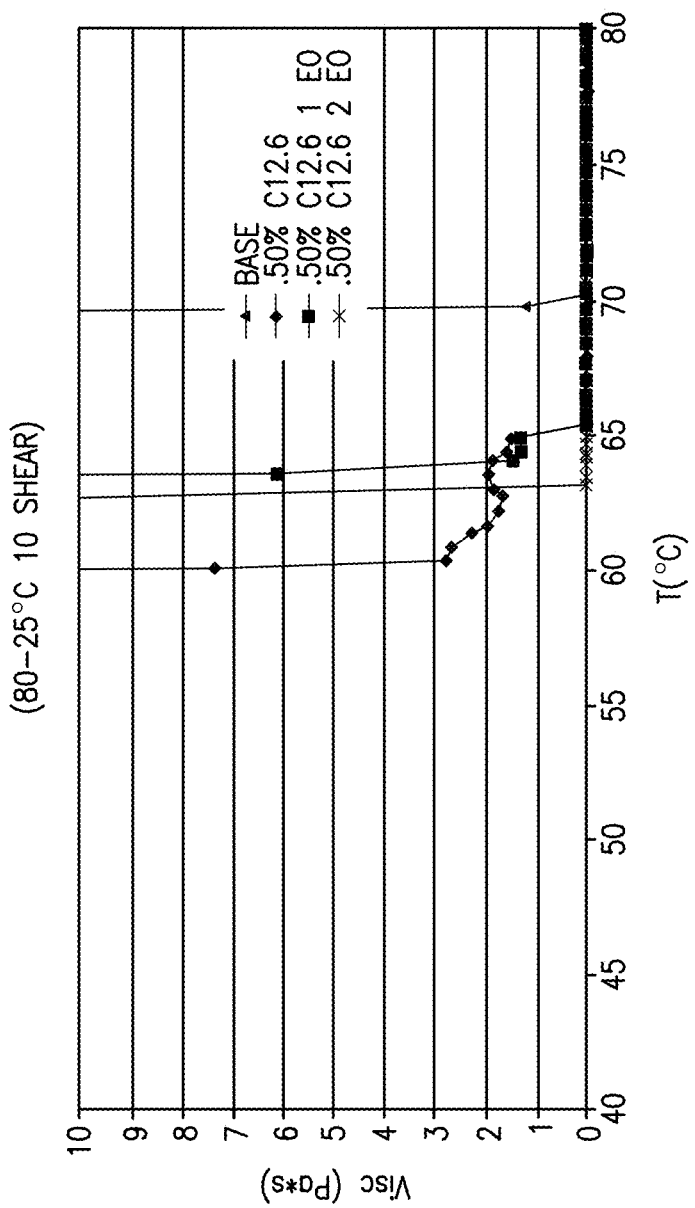
FIG. 8 is a graph showing that when ethoxylation is added to the blend of linear primary alcohols, the phase transition region between the liquid phase and the cubic phase is eliminated with minimal effect on the overall gel point suppression. At 1 mole of ethoxylation (1EO), the phase transition region is greatly reduced. At 2 moles of ethoxylation (2EO), the phase transition region is eliminated.

As shown in FIG. 7, as the amount of primary alcohol blend is increased, the phase transition region described above becomes a more significant consideration. As shown in FIG. 8, in formulation where the presence of a phase transition region is a concern, the use of an ethoxylated linear primary alcohol blend serves to eliminate this phase transition area with minimal effect on the desired overall gel point suppression. As shown in FIG. 8, at 1 mole ethoxylation, the phase transition is greatly reduced, and at 2 moles ethoxylation, the phase transition is eliminated. The four formulas tested, for which the results are shown in FIG. 8, include no alcohol (BASE), 0.5% by wt. primary alcohol blend with an average carbon chain length of 12.6 (C12.6); 0.5% by wt. ethoxylated primary alcohol blend with an average carbon chain length of 12.6 and average 1 mole ethylene oxide (EO) per mole of alcohol (C12.6 1 EO), and 0.5% by wt. ethoxylated primary alcohol blend with an average carbon chain length of 12.6 and average 2 mole EO per mole of alcohol (C12.6 2 EO).

zero ethoxylation and with 2 moles of ethylene oxide per mole of alcohol. The data charted is as follows:

| % Alcohol | Gel Point Shift | |
|---|---|---|
| | 0 EO | 2 EO |
| 0.25 | 0 | 1.9 |
| 0.5 | 9.4 | 6.7 |
| 0.75 | 13.7 | 8.9 |

Test data as to formulas containing certain linear primary alcohol blends and ethoxylated linear primary alcohol blends are set forth in the Table below. The components of the formulas were the same except for the alcohol blend present. A Base formula containing no alcohol is also present as a control. The same test methods were used as to each formula to allow for comparison as to the data set forth.

| Trade Name | Average Chain Length | EO | Amount | Adhesion | FTA | Max Viscosity | Gel Point | Phase Transition Point | Gel Point Shift | Phase Transition |
|---|---|---|---|---|---|---|---|---|---|---|
| Base (No Alcohol) | NA | NA | 0.00% | 20.00 | 12.6 | 294 | 69.7 | 70.2 | | 0.5 |
| NEODOL 23 | 12.6 | 0 | 0.50% | 16.25 | 12.5 | 266 | 60.3 | 65.4 | −9.4 | 5.1 |
| NEODOL 23-1 | 12.6 | 1 | 0.50% | 18.00 | 12.1 | 287 | 64.0 | 65.4 | −5.7 | 1.4 |
| NEODOL 23-2 | 12.6 | 2 | 0.50% | 18.25 | 12.4 | 282 | 63.0 | 63.0 | −6.7 | 0.0 |
| NEODOL 1 | 11.0 | 0 | 0.50% | 17.50 | 12.0 | 289 | 63.0 | 65.4 | −6.7 | 2.4 |
| NEODOL 45 | 14.5 | 0 | 0.50% | 17.75 | 12.8 | 280 | 62.1 | 66.2 | −7.6 | 4.1 |
| NEODOL 23 | 12.6 | 0 | 0.25% | 19.50 | 12.5 | 263 | 70.6 | 71.1 | 0.9 | 0.5 |
| NEODOL 23 | 12.6 | 0 | 0.75% | 15.50 | 12.5 | 259 | 56.0 | 66.2 | −13.7 | 10.2 |
| NEODOL 23-2 | 12.6 | 2 | 0.25% | 18.75 | 12.4 | 277 | 67.8 | 67.8 | −1.9 | 0.0 |
| NEODOL 23-2 | 12.6 | 2 | 0.75% | 16.75 | 12.3 | 259 | 60.8 | 67.6 | −8.9 | 6.8 |

FTA = Force to actuate
EO = Ethylene Oxide

Figure 9:
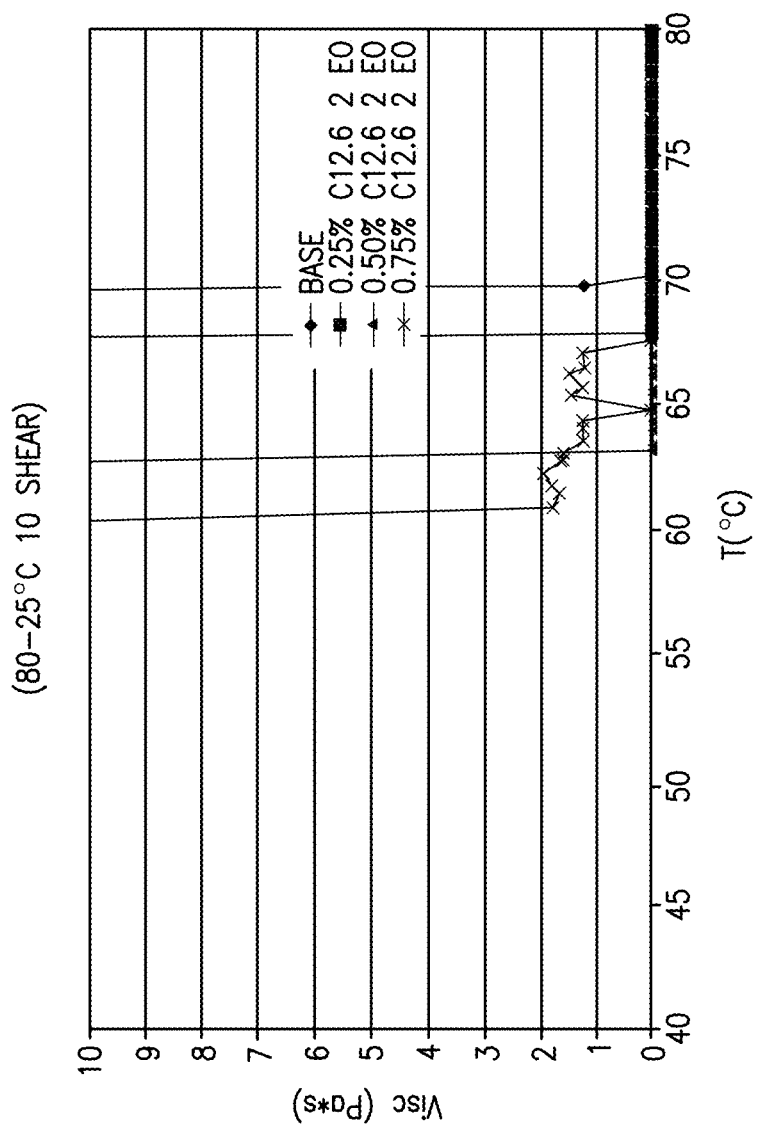
FIG. 9 is a graph showing the effect on the phase transition region in relation to varying the amount of ethoxylated linear primary alcohol blend. When the amount of the 2 mole ethoxylated linear primary alcohol blend is increased from 0.25% or 0.5% to 0.75%, a phase transition region is again formed. Upon a further increase in ethoxylation, the phase transition region should again be eliminated.

As shown in FIG. 9, when the amount of the 2 mole ethoxylated primary alcohol as shown in FIG. 8 is increased to 0.75% by wt., a phase transition region is again formed. Upon further increase in ethoxylation, this phase transition region should be eliminated.

Figure 10:
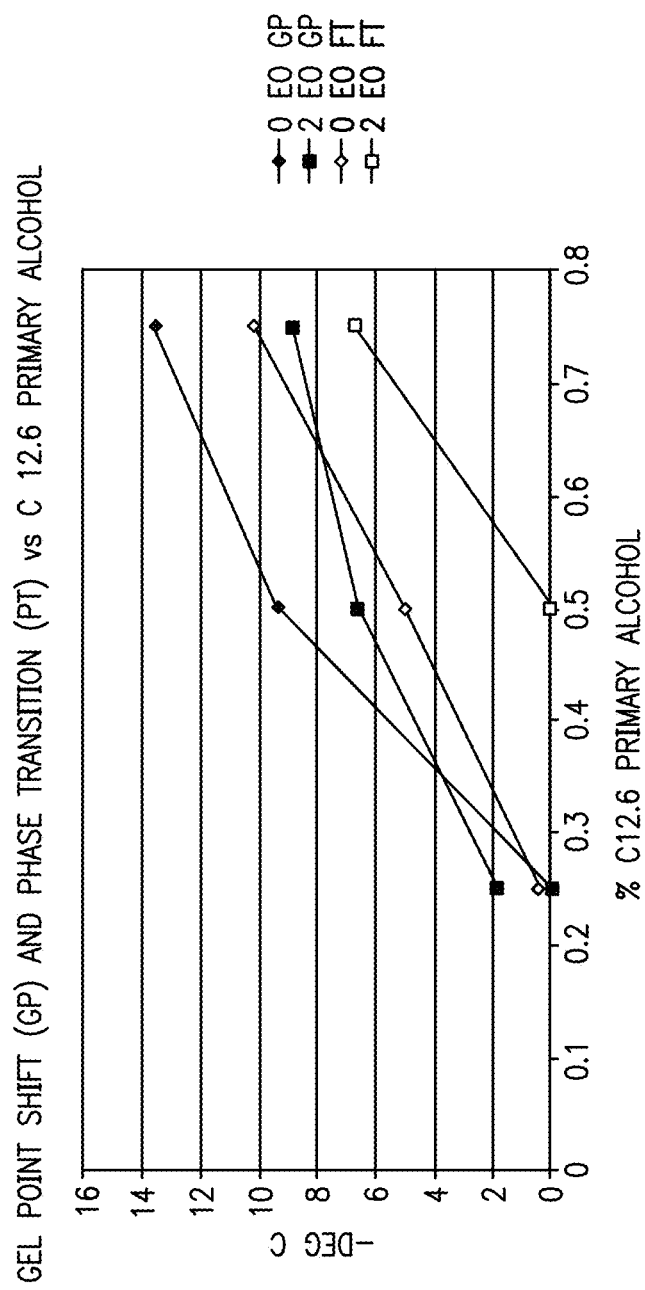
FIG. 10 is a graph summarizing the gel point shift (GP) and phase transition (PT) area for a blend of primary alcohols having chain lengths with an average of 12.6 carbons.

FIG. 10 summarizes the gel point shift and phase transition area for the primary alcohol blend having an average of 12.6 carbons in the chain length. The data of FIG. 10 is as follows:

| % Alcohol | Gel Point Shift | | Phase Transition | |
|---|---|---|---|---|
| | 0 EO GP | 2 EO GP | EO | 2 EO PT |
| 0.25 | 0 | 1.9 | 0.5 | 0 |
| 0.5 | 9.4 | 6.7 | 5.1 | 0 |
| 0.75 | 13.7 | 8.9 | 10 | 6.8 |

Figure 11:
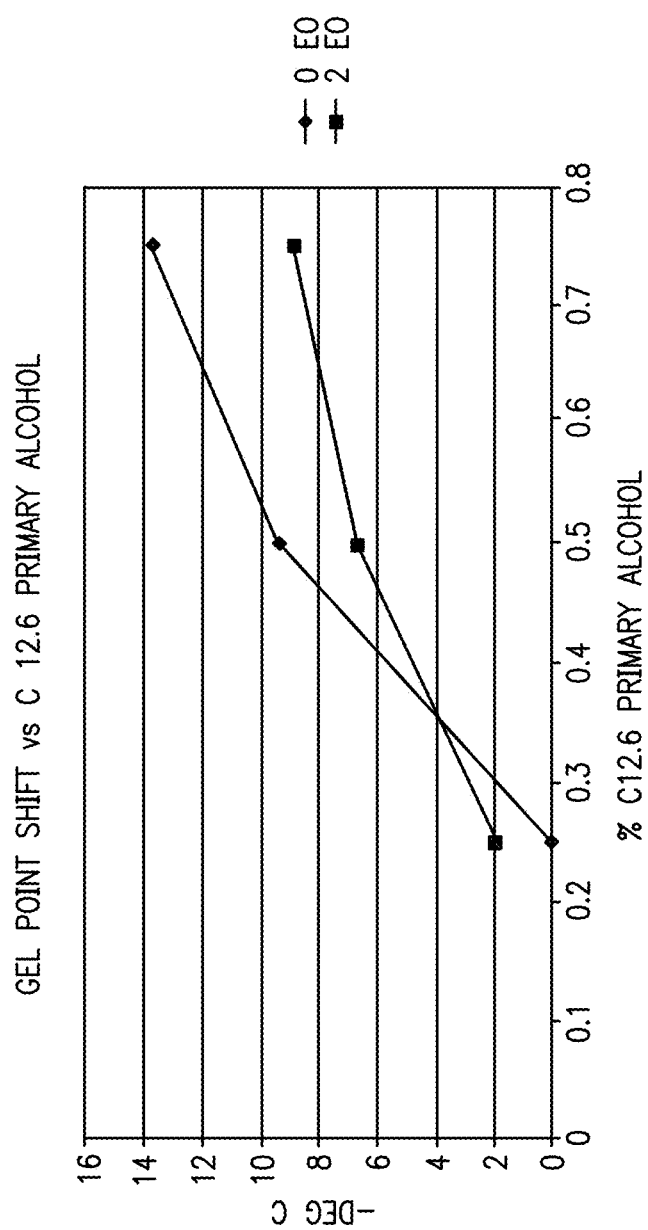
FIG. 11 is a graph showing a comparison of a blend of primary alcohols having an average chain length of 12.6 carbons without ethoxylation (0EO) and with 2 moles of ethoxylation (2EO).

FIG. 11 shows the gel point shift as to the % of a primary alcohol blend with an average 12.6 carbon chain length, with The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention.

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

All documents cited in the Detailed Description of the invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

We claim:

1. A cleaning composition for use on a hard surface, the composition comprising:
   (a) about 10 to 40 wt. % of at least one adhesion promoter, which includes a polyalkoxy substituted compound having 25 to 45 ethoxy groups;
   (b) at least about 7.5 wt. % of at least one nonionic surfactant, which can serve all or in part as the at least one adhesion promoter; and
   (c) greater than 0 to about 2 wt. % of a blend of non-ethoxylated linear primary alcohols wherein each alcohol of the non-ethoxylated blend includes a carbon chain containing 9 to 17 carbons, or an ethoxylated blend of linear primary alcohols wherein each alcohol of said ethoxylated blend includes a carbon chain containing 9 to 17 carbons;
   wherein the composition is a gel having a transport rate factor of less than about 55 seconds and a gel temperature of about 50 to 80° C.; the composition has an adhesion time of greater than about 8 hours; and
   the composition is structured to self-adhere to a hard surface to which the composition is applied and to transport a portion of said composition along the hard surface in a 360 degree extended area outward from an area of initial product application on the hard surface.

2. The composition of claim 1, wherein the polyalkoxy substituted compound further comprises a hydrophobic residual.

3. The composition of claim 2, wherein the hydrophobic residual is an alkyl residual having an alkyl chain length of 16 to 30 carbon atoms.

4. The composition of claim 1, wherein the polyalkoxy substituted compound comprises an ethoxylated alcohol.

5. The composition of claim 1, further comprising one or more cationic surfactants.

6. The composition of claim 1, wherein the composition has a transport rate factor of about 30 seconds to about 55 seconds.

7. The composition of claim 1, wherein the composition has a transport rate factor of about 30 seconds to about 40 seconds.

8. The composition of claim 1, wherein the composition comprises about 15 to 35 wt. % of the adhesion promoter and the polyalkoxy substituted compound includes ethoxylated alcohol.

9. The composition of claim 1, wherein the composition further comprises greater than 0 to about 15 wt. % of at least one fragrance.

10. The composition of claim 1, wherein the composition comprises greater than 0 to about 2 wt. % of the non-ethoxylated blend of linear primary alcohols.

11. The composition of claim 1, wherein the composition comprises greater than 0 to about 2 wt. % of the ethoxylated blend of linear primary alcohols.

12. The composition of claim 1, wherein the composition further comprises greater than 0 to about 3.5 wt. % non-polar hydrocarbon.

13. The composition of claim 12, wherein the non-polar hydrocarbon comprises mineral oil.

14. The composition of claim 1, wherein the polyalkoxy substituted compound comprises an ethoxylated $C_{16}$ alcohol, ethoxylated $C_{16}$ alcohol and/or ethoxylated $C_{22}$ alcohol.

15. The composition of claim 1, wherein the polyalkoxy substituted compound comprises ethoxylated alcohol having a hydrophobic residual with at least 12 carbon atoms.

16. The composition of claim 1, wherein the at least one adhesion promoter further comprises polysaccharide.

17. The composition of claim 1, wherein the polyalkoxy substituted compound comprises C16-18 ethoxylated alcohol having 25 to 45 ethoxy groups.

18. The composition of claim 1, wherein the composition comprises at least about 20 wt. % of the at least one adhesion promoter; and at least about 40 wt. % water; and further comprises greater than 0 to about 3 wt. % non-polar hydrocarbon; and about 1 to 12 wt. % glycerin.

19. The composition of claim 1, wherein the composition further comprises alkylene glycol and/or glycerin.

20. The composition of claim 1, wherein the polyalkoxy substituted compound comprises polyethylene glycol.

21. The composition of claim 1, wherein the composition comprises about 1 to 12 wt. % glycerin.

22. The composition of claim 1, further comprising at least one active agent, wherein the active agent is a germicide, antimicrobial, bleach, deodorizer, chelator or combination thereof.

23. The composition of claim 1, wherein each ethoxylated alcohol in the ethoxylated blend includes an average of 1 to 9 moles of ethylene oxide.

24. A cleaning composition for use on a hard surface, the composition comprising:
   (a) about 10 to 40 wt. % of at least one adhesion promoter, which includes polyalkoxy substituted compound having 25 to 45 ethoxy groups;
   (b) at least about 7.5 wt. % of at least one nonionic surfactant, which can serve all or in part as the at least one adhesion promoter; and
   (c) greater than 0 to about 2 wt. % of a blend of non-ethoxylated linear primary alcohols wherein each alcohol of the non-ethoxylated blend includes a carbon chain containing 9 to 17 carbons;
   wherein the composition is a gel having a transport rate factor of less than about 55 seconds and a gel temperature of about 50 to 80° C.; the composition has an adhesion time of greater than about 8 hours; and
   the composition is structured to self-adhere to a hard surface to which the composition is applied and to transport a portion of said composition along said hard surface in a 360 degree extended area outward from an area of initial product application on the hard surface.

25. A cleaning composition for use on a hard surface, the composition comprising:
   (a) about 10 to 40 wt. % of at least one adhesion promoter, which includes polyethoxy compound having 25 to 45 ethoxy groups;
   (b) at least about 7.5 wt. % of at least one nonionic surfactant, which can serve all or in part as the at least one adhesion promoter; and (c) greater than 0 to about 2 wt. % of an ethoxylated blend of linear primary alcohols wherein each alcohol of said ethoxylated blend includes a carbon chain containing 9 to 17 carbons, and each ethoxylated alcohol in the blend includes an average of 1 to 9 moles of ethylene oxide;

wherein the composition is a gel having a transport rate factor of less than about 55 seconds and a gel temperature of about 50 to 80° C.; the composition has an adhesion time of greater than about 8 hours; and the composition is structured to self-adhere to a hard surface to which the composition is applied and to transport a portion of said composition along said hard surface in a 360 degree extended area outward from an area of initial product application on the hard surface.

26. The composition of claim 25, further comprising one or more cationic surfactants, and a non-polar hydrocarbon.

* * * * *